United States Patent [19]

Hindsgaul

[11] Patent Number: 5,780,603
[45] Date of Patent: Jul. 14, 1998

[54] COMBINATORIAL SYNTHESIS OF CARBOHYDRATE LIBRARIES

[75] Inventor: Ole Hindsgaul, Edmonton, Canada

[73] Assignee: Synsorb Biotech, Inc., Alberta, Canada

[21] Appl. No.: 751,231

[22] Filed: Nov. 15, 1996

[51] Int. Cl.$^6$ .......................... C07H 15/14; A61K 31/70
[52] U.S. Cl. .......................... 536/4.1; 536/18.5; 536/18.6; 536/122; 514/24
[58] Field of Search .......................... 536/4.1, 18.5, 536/18.6, 122; 514/24

[56] References Cited

U.S. PATENT DOCUMENTS

| | | | |
|---|---|---|---|
| 5,079,353 | 1/1992 | Ratcliffe et al. | 536/53 |
| 5,143,854 | 9/1992 | Pirrung et al. | 436/518 |

FOREIGN PATENT DOCUMENTS

WO96/06102  2/1992  WIPO.

OTHER PUBLICATIONS

Ferrier et al. *Carbohydrate Chemistry* 1996, 28, 158–64. month not available.

Ferrier et al. *Carbohydrate Chemistry* 1993, 27, 140–47. month not available.

Williams et al. *Carbohydrate Chemistry* 1983, 17, 116–19. month not available.

Horton et al. Thio Sugars and Derivatives, In "The Carbohydrates: Chemistry and Biochemistry", 2nd edition, Pigman et al., eds., Academic Press, New York, 1980. month not available.

Schnabelrauch et al. *Helv. Chim. Acta* 1994, 77, 778. month not available.

Collins et al. "Monosaccharides: Their Chemistry and Their Roles in Natural Products" John Wiley & Sons, Chichester, England, 1995. pp. 97–106. month not available.

Hol, W. G. J. et al., "Structure and Function of *E. coli* Heat–Labile Enterotoxin and Cholera Toxin B Pentamer", *Bacterial Toxins and Virulence Factors in Disease*, Ed. by J. Moss et al., Marcel Dekker, Inc. (1995). month not available.

Spangler, B. D., "Structure and Function of Cholera Toxin and Related *Escherichia coli* Heat–Labile Enterotoxin", *Microbiological Reviews*, 56(4):622–647 (1992). month not available.

Evans et al., "The Asymmetric Synthesis of α–Amino Acids. Electrophilic Azidation of Chiral Imide Enolates, a Practical Approach to the Synthesis of (R)– and (S)–α–Azido Carboxylic Acids", *J. Amer. Chem. Soc.*, 112:4011–4030 (1990). month not available.

Williams, R. et al., "Asymmetric Synthesis of Monosubstituted and α,α–Distributed α–Amino Acids via Diastereoselective Glycine Enolate Alkylations", *J. Amer. Chem. Soc.*, 113:9276–9286 (1991). month not available.

J. Defaye et al., "Thiooligosaccharides: Their Synthesis and Reactions with Enzymes" in *Studies in Natural Products Chemistry*, vol. 8, pp. 315–357, Elsevier Sciences Publishers (1991). month not available.

J.M. Kerr et al., "Encoded Cominatorial Peptide Libraries Containing Non–Natural Amino Acids", *J. Am. Chem. Soc.*, 115:2529 (1993). month not available.

M.C. Needels et al., "Generation and screening of an oligonucleotide–encoded synthetic peptide library", *Proc. Natl. Acad. Sci.*, USA, 90:10700 (1993). month not available.

M.H.J. Ohlmeyer et al., "Complex synthetic chemical libraries indexed with molecular tags", *Proc. Natl. Acad. Sci. USA*, 90:10922 (1993). month not available.

Svennerholm, A–M. et al., Identification of *Escherichia coli* Heat–Labile Enterotoxin by Means of a Ganglioside Immunosorbent Assay ($G_{M1}$–ELISA) Procedure, *Current Microbiology*, 1:19–23 (1978). month not available.

*Primary Examiner*—Kathleen K. Fonda
*Attorney, Agent, or Firm*—Burns, Doane, Swecker & Mathis, L.L.P.

[57] ABSTRACT

Disclosed are methods for synthesizing very large collections of diverse thiosaccharide derivatives optionally attached to a solid support. Also disclosed are libraries of diverse thiosaccharide derviatives.

11 Claims, 2 Drawing Sheets

COMBINATORIAL SYNTHESIS OF CARBOHYDRATE LIBRARIES

BACKGROUND OF THE INVENTION

1. Field of the Invention

This invention is directed to methods for synthesizing very large collections of diverse thiosaccaride derivatives optionally attached to a solid support. This invention is further directed to a library of diverse thiosaccaride derivatives.

2. References

The following publications, patents and patent applications are cited in this application as superscript numbers:

[1] International Patent Application Publication No. WO 93/06121.

[2] U.S. Pat. No. 5,143,854, issued Sep. 1, 1992.

[3] Hol, W. G. J., et al., "Structure and Function of E. coli Heat-Labile Enterotoxin and Cholera Toxin B Pentamer", *Bacterial Toxins and Virulence Factors in Disease*, Ed. by J. Moss et al., Marcel Dekker, Inc. (1995).

[4] Spangler, B. D., "Structure and Function of Cholera Toxin and Related *Escherichia coli* Heat-Labile Enterotoxin", *Microbiological Reviews*, 56(4):622–647 (1992).

[5] Williams (ed.), *Synthesis of Optically Active α-Amino Acids*, Pergamon Press (1989).

[6] Evans et al., *J. Amer. Chem. Soc.*, 112:4011–4030 (1990).

[7] Pu et al., *J. Amer. Chem. Soc.*, 56:1280–1283 (1991).

[8] Williams et al., *J. Amer. Chem. Soc.*, 113:9276–9286 (1991).

[9] Ratcliffe, et al., U.S. Pat. No. 5,079,353.

[10] J. Defaye, et al., "Thiooligosaccharides: Their Synthesis and Reactions with Enzymes" in *Studies in Natural Products Chemistry*, Vol. 8, pp. 315–357, Elsevier Sciences Publishers (1991).

[11] J. M. Kerr, S. C. Banville and R. N. Zuckermann, *J. Am. Chem. Soc.*, 115:2529 (1993).

[12] V. Nikolaiev, A. Stierandova, V. Krchnak, B. Seligmann, K. S. Lam, S. E. Salmon and M. Lebl, *Pept. Res.*, 6:161 (1993)

[13] M. C. Needels, D. G. Jones, E. M. Tate, G. L. Heinkel, L. M. Kochersperger, W. J. Dower, R. W. Barrett and M. A. Gallop, *Proc. Natl. Acad. Sci.*, USA, 90:10700 (1993)

[14] M. H. J. Ohlmeyer, R. N. Swanson, L. W. Dillard, J. C. Reader, G. Asouline, R. Kobayashi, M. Wigler and W. C. Still, *Proc. Natl. Acad. Sci.* USA, 90:10922 (1993)

[15] Svennerholm, A-M. et al., *Current Microbiology*, 1:19–23 (1978).

All of the above publications, patents and patent applications are herein incorporated by reference in their entirety to the same extent as if each individual publication, patent or patent application was specifically and individually indicated to be incorporated by reference in its entirety.

3. State of the Art

Compounds having biological activity can be identified by screening diverse collections of compounds (i.e., libraries of compounds) produced through either molecular biological or synthetic chemical techniques. Such screening methods include methods wherein each member of the library is tagged with a unique identifier tag to facilitate identification of compounds having biological activity or where the library comprises a plurality of compounds synthesized at specific locations on the surface of a solid substrate wherein a receptor is appropriately labeled to identify binding to the compound, e.g., fluorescent or radioactive labels. Correlation of the labelled receptor bound to the substrate with its location on the substrate identifies the binding compound.[2]

Central to these methods is the screening of a multiplicity of compounds in the library and the ability to identify the structures of the compounds which have a requisite biological activity. Preferably, in order to facilitate synthesis and identification, the compounds in the library are typically formed on solid supports wherein the compound is covalently attached to the support via a cleavable or non-cleavable linking arm. In this regard, libraries of diverse compounds are prepared and then screened to identify "lead compounds" having good binding affinity to the receptor.

Pharmaceutical drug discovery relies heavily on studies of structure-activity relationships wherein the structure of "lead compounds" is typically altered to determine the effect of the alteration on activity. Alteration of the structure of the lead compounds permits evaluation of the effect of the structural alteration on activity. Thus libraries of compounds derived from a lead compound can be created by including derivatives of the lead compound and repeating the screening procedures.

Ideally, the compounds are synthesized in situ on the solid support so that the support can be tagged to identify the synthetic steps employed and/or the derivative incorporated onto the support. However, relatively simple synthetic methods to produce a diverse collection of such derivatives on the supports are often not available.

One particular class of compounds which would be useful for inclusion in screening libraries is thiosaccharide derivatives. It is well known that certain toxins and microorganisms bind to oligosaccharide receptors on host cells as an initial step in the pathological development of various disease conditions.[3] For example, heat-labile enterotoxin ("LT"), secreted by certain enterotoxigenic strains of *Escherichia coli*, and cholera toxin ("CT"), produced by *Vibrio cholerae*, are known to bind to ganglioside $G_{M_1}$, a glycosphingolipid situated in the outer leaflet of the host cell membrane and which has a characteristic pentasaccharide structure, i.e., Gal(β1→3)GalNAc(β1→4){NeuAc(α2→3)}Gal(β1→4)Glc, on its surface.[3] LT has been identified as one of the causative agents of bacterial-induced traveller's diarrhea[4] and CT is known to be the causative agent of the severe diarrheal disease, cholera.[4]

Additionally, enterovirulent microorganisms (e.g., bacteria, virus, fungi, and the like) such as *Vibrio cholerae* and enterotoxigenic strains of *Escherichia coli* can directly bind to cell surface receptors forming a colony at the point of attachment. Such binding is detrimental because it permits expressed toxin to immediately interact with the cell surface.

Accordingly, in order to develop new pharmaceutical drugs to treat various disease conditions, it would be highly desirable to be able to generate very large libraries of diverse thiosaccharide derivatives.

SUMMARY OF THE INVENTION

This invention is directed to general synthetic methods for generating very large libraries of diverse thiosaccharide derivatives optionally attached to a solid support. The thiosaccharide derivative libraries provided by this invention are synthesized by reacting a thiosaccharide with a Michael acceptor or an α-halocarbonyl compound to provide for a thiosaccharide carbonyl compound. The carbonyl group of the thiosaccharide carbonyl compound can optionally be reduced to provide for a plurality of alcohol and/or amine thiosaccharide derivatives. In one embodiment, the alcohol and/or amine group of the thiosaccharide derivative is further derivatized to provide for a plurality of thiosaccharide derivatives.

In one embodiment of this invention, the thiosaccaride derivatives are covalently attached to a solid support. Solid supports containing such thiosaccharide derivatives preferably comprise a linking arm which links the solid support to the thiosaccharide derivative. The linking arm can be either cleavable or non-cleavable and when cleavable, can be used to prepare a library of either solid phase or soluble thiosaccharide derivatives. The library of thiosaccharide derivatives, whether soluble or insoluble, can be screened to isolate individual compounds that possess some desired biological activity. In a preferred embodiment, each compound in the library is unique.

Accordingly, in one of its method aspects, this invention is directed to a method for synthesizing a thiosaccharide derivative, which method comprises:

(a) providing a thiosaccharide;

(b) providing at least a stoichiometric amount of a coupling reagent selected from the group consisting of Michael acceptors and α-halocarbonyl compounds; and (c) contacting the thiosaccharide and the coupling reagent under conditions which provide for a thiosaccharide carbonyl compound.

In another of its method aspects, this invention is directed to a method for synthesizing a thiosaccharide derivative on a solid support, which method comprises:

(a) providing a thiosaccharide;

(b) providing at least a stoichiometric amount of a coupling reagent selected from Michael acceptors and α-halocarbonyl compounds wherein either the thiosaccharide or the coupling reagent is covalently attached to a solid support; and (c) contacting the thiosaccharide and the coupling reagent under conditions which provide for a thiosaccharide carbonyl compound covalently attached to a solid support.

In preferred embodiments of this invention, each of the above methods for synthesizing a thiosaccharide derivative further comprises reducing the carbonyl group of the thiosaccharide carbonyl compound to form a group selected from hydroxy and amino derivatives. Optionally, the hydroxy or amino group can be further derivatized to form a group selected from esters, amides, carbamates, ureas, thiourea, thioesters and thiocarbamates.

In still another of its method aspects, this invention is directed to a method for preparing a thiosaccharide derivative library produced by synthesizing on each of a plurality of solid supports a single compound wherein each compound comprises a thiosaccharide derivative, which library is synthesized in a process comprising:

a) apportioning solid supports among a plurality of reaction vessels which supports comprise a reactive functional group covalently bound thereto which group is capable of covalently binding a thiosaccharide at a position other than the thiol group;

b) contacting the supports in each reaction vessel with a unique thiosaccharide under conditions wherein the thiosaccharide is covalently attached to the solid supports through the reactive functional group;

c) pooling the supports;

d) apportioning the supports from (c) above among a plurality of reaction vessels; and e) contacting the supports in each reaction vessel from (d) above with a unique coupling reagent selected from the group consisting of Michael acceptors and α-halocarbonyl compounds under conditions which provide for a thiosaccharide carbonyl compound covalently bound to said support.

And, in yet another of its method aspects, this invention is directed to a method for preparing a thiosaccharide derivative library produced by synthesizing on each of a plurality of solid supports a single compound wherein each compound comprises a thiosaccharide derivative, which library is synthesized in a process comprising:

a) apportioning solid supports among a plurality of reaction vessels which supports comprise a reactive functional group covalently bound thereto which group is capable of covalently binding a coupling reagent;

b) contacting the supports in each reaction vessel with a unique coupling reagent selected from the group consisting of Michael acceptors and α-halocarbonyl compounds under conditions wherein the coupling reagent is covalently attached to the solid supports through the reactive functional group;

c) pooling the supports;

d) apportioning the supports from (c) above among a plurality of reaction vessels; and e) contacting the supports in each reaction vessel from (d) above with a unique thiosaccharide under conditions which provide for a thiosaccharide carbonyl compound covalently bound to said support.

In preferred embodiments of this invention, each of the above methods for preparing a thiosaccharide derivative library exemplified in procedures (a) through (e) further comprises: (f) pooling the supports from procedure (e); (g) apportioning the supports from (f) above among a plurality of reaction vessels; and (h) reducing the carbonyl group of the thiosaccharide carbonyl compound to form a group selected from hydroxy and amino derivatives. Still further, such methods optionally include the further steps of: (i) pooling the supports from procedure (h) above; (j) apportioning the supports from (i) above among a plurality of reaction vessels; and (k) derivatizing the hydroxyl or amine groups to form a functional group selected from esters, amides, carbamates, ureas, thioureas, thioesters and thiocarbamates.

The methods described above can be used to create a library of diverse thiosaccharide derviatives. Accordingly, in one of its composition aspects, this invention is directed to a library of diverse thiosaccharide derivatives comprising a plurality of solid supports having a plurality of covalently bound thiosaccharides derivatives, wherein the thiosaccharide derivative bound to each of said supports is substantially homogeneous and further wherein the thiosaccharide derivative bound on one support is different from the thiosaccharide derivatives bound on the other supports and further wherein said thiosaccharide derivative is represented by the formula (I):

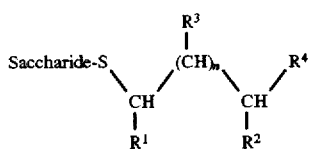

wherein $R^1$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I to the solid support;

R² is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I to the solid support;

R³ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I to the solid support;

wherein R¹ and R² or R¹ and R³ or R² and R³ can be joined, together with the carbon atoms to which R¹ and/or R² and/or R³ are attached, to form a cycloalkyl ring, a cycloalkenyl ring, or a heterocyclic ring, provided that said heterocyclic ring is not a saccharide or an oligosaccharide;

R⁴ is selected from the group consisting of —XR⁵, —XC(O)R⁶, —XC(O)X'R⁷ and —C(O)XR⁸;

wherein X and X' are each independently selected from the group consisting of oxygen, sulfur and —NR⁹—, wherein R⁹ is selected from the group consisting of hydrogen and alkyl;

R⁵ is selected from the group consisting of hydrogen, alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I to the solid support, and when X is —NR⁹—, then R⁹ together with X can form an amino acid;

R⁶ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I to the solid support;

R⁷ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I to the solid support;

R⁸ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I to the solid support; and n is an integer equal to 0 or 1;

wherein the saccharide is selected from the group consisting of a monosaccharide, an oligosaccharide, monosaccharide-Y and oligosaccharide-Y, wherein Y is a linking arm covalently linking the compound of formula I to the solid support;

with the proviso that only one of R¹, R², R³, R⁴, R⁶, R⁷, R⁸ and Y is linked to the solid support.

DETAILED DESCRIPTION OF THE INVENTION

Figure 1:
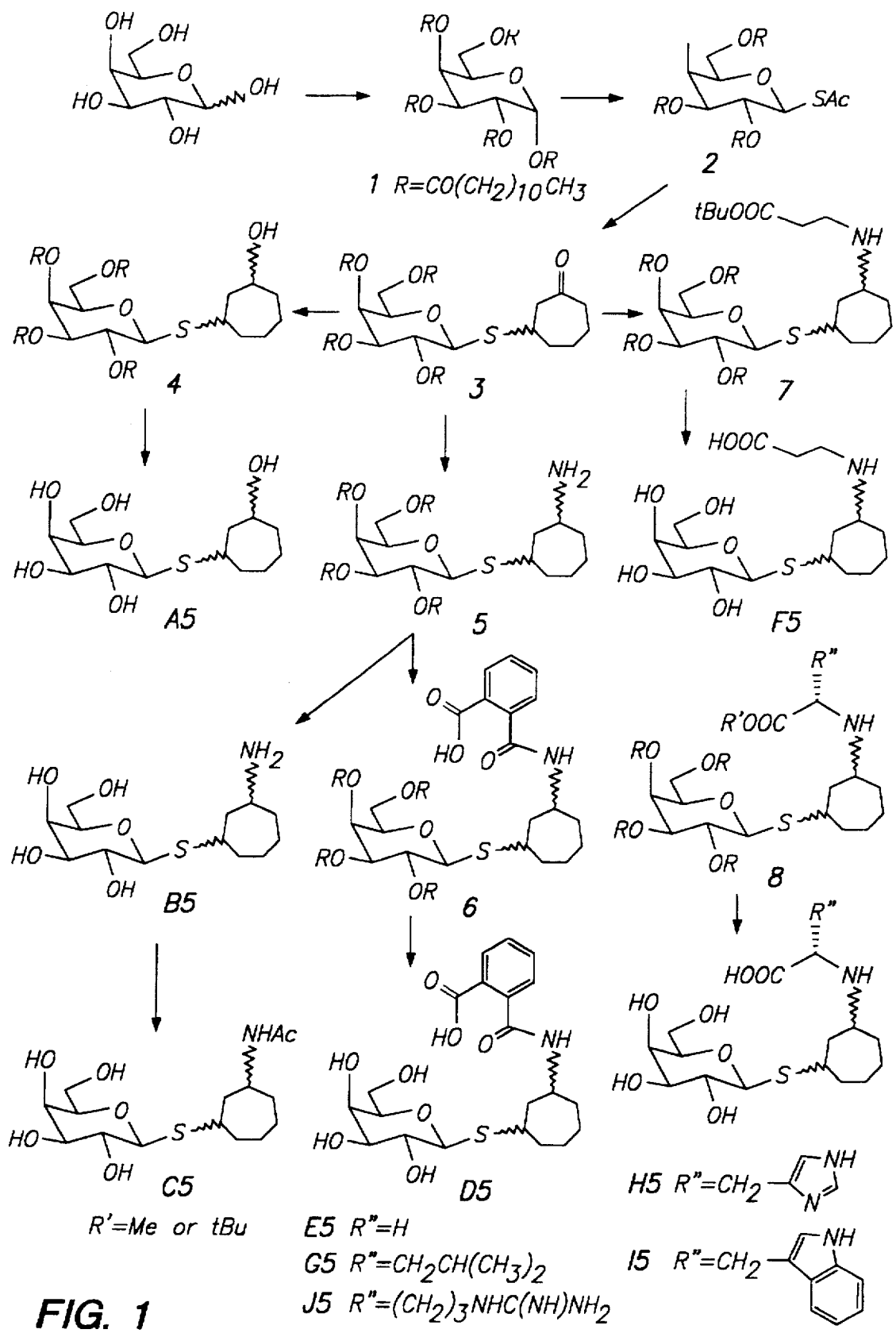
FIG. 1 illustrates a preferred reaction scheme for synthesizing a library of diverse thiosaccharide derivatives using an α,β-unsaturated carbonyl compound, i.e., cyclohept-2-en-1-one.

This invention is directed to libraries of diverse thiosaccharide derivatives optionally attached to a solid support and to methods for generating such libraries. However, prior to describing this invention in further detail, the following terms will first be defined.

Definitions

"Acyl" refers to the groups alkyl-C(O)—, aryl-C(O)—, and heteroaryl-C(O)— where alkyl, aryl and heteroaryl are as defined herein.

"Acylamino" refers to the group —C(O)NRR where each R is independently hydrogen or alkyl.

"Acyloxy" refers to the groups alkyl-C(O)O—, aryl-C(O)O—, heteroaryl-C(O)O—, and heterocyclic-C(O)O— where alkyl, aryl, heteroaryl and heterocyclic are as defined herein.

"Alkaryl" refers to -alkylene-aryl groups preferably having from 1 to 8 carbon atoms in the alkylene moiety and from 6 to 10 carbon atoms in the aryl moiety. Such alkaryl groups are exemplified by benzyl, phenethyl and the like.

"Alkoxy" refers to the group alkyl-O—. Such alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkoxyalkyl" refers to the group -alkylene-O-alkyl which includes by way of example, methoxymethyl ($CH_3OCH_2$—), methoxyethyl ($CH_3$—O—$CH_2CH_2$—) and the like.

"Alkenyl" refers to alkenyl groups preferably having from 2 to 8 carbon atoms and more preferably 2 to 6 carbon atoms and having at least 1 and preferably from 1–2 sites of alkenyl unsaturation. Such alkenyl groups include ethenyl (—CH=CH₂), n-propenyl (i.e., allyl) (—CH₂CH=CH₂), iso-propenyl (—C(CH₃)=CH₂), and the like.

"Alkyl" refers to monovalent alkyl groups preferably having from 1 to 8 carbon atoms and more preferably 1 to 6 carbon atoms. This term is exemplified by groups such as methyl, ethyl, n-propyl, iso-propyl, n-butyl, iso-butyl, n-hexyl, and the like.

"Substituted alkyl" refers to a branched or straight chain alkyl group of from 1 to 8 carbon atoms having from 1 to 3 substituents selected from the group consisting of hydroxy, acyl, acylamino, acyloxy, alkoxy, alkenyl, alkynyl, amino, aminoacyl, aryl, aryloxy, carboxy, carboxyalkyl, cyano, cycloalkyl, guanidino, halo, heteroaryl, heterocyclic, nitro, thiol, thioaryloxy, thioheteroaryloxy, and the like. Preferred substituents include hydroxy and amino.

"Alkylene" refers to divalent alkylene groups preferably having from 1 to 8 carbon atoms and more preferably 1 to 6 carbon atoms. This term is exemplified by groups such as methylene (—CH₂—), ethylene (—CH₂CH₂—), the propylene isomers (e.g., —CH₂CH₂CH₂— and —CH(CH₃)CH₂—) and the like.

"Alkynyl" refers to alkynyl groups preferably having from 2 to 8 carbon atoms and more preferably 2 to 6 carbon atoms and having at least 1 and preferably from 1–2 sites of alkynyl unsaturation. Such alkynyl groups include ethynyl (—CH≡—CH₂), propargyl (—CH₂CH=CH₂) and the like.

"Amino acid" refers to any of the naturally occurring amino acids, as well as synthetic analogs and derivatives thereof. α-Amino acids comprise a carbon atom to which is bonded an amino group, a carboxy group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine). One of skill in the art will appreciate that the term "amino acid" can also include β-, γ-, δ-, and ω-amino acids, and the like. Unnatural amino acids are also known in the art, as set forth in, for example, Williams[5], Evans et al.[6], Pu et al.[7], Williams et al.[8], and all references cited therein. Stereoisomers (e.g., D-amino acids) of the twenty conventional amino acids, unnatural amino acids such as α,α-disubstituted amino acids and other unconventional amino acids may also be suitable components for compounds of the present invention. Examples of unconventional amino acids include: 4-hydroxyproline, 3-methylhistidine, 5-hydroxylysine, and other similar amino acids and imino acids (e.g., 4-hydroxyproline).

"Aminoacyl" refers to the group —NRC(O)R where each R is independently hydrogen or alkyl.

The term "amino derivative(s)" refers to a primary, secondary or tertiary amine compound produced by reductive amination of a thiosaccharide carbonyl compound in the presence of ammonia or an amine, including amino acids and derivatives thereof.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

Unless otherwise constrained by the definition for the aryl substituent, such aryl groups can optionally be substituted with from 1 to 3 substituents selected from the group consisting of hydroxy, acyl, acyloxy, alkyl, alkoxy, alkenyl, alkynyl, amino, aminoacyl, aryl, aryloxy, carboxy, carboxyalkyl, cyano, halo, nitro, heteroaryl, trihalomethyl and the like. Preferred substituents include alkyl, alkoxy, halo, carboxy, cyano, nitro, trihalomethyl, and thioalkoxy.

"Aryloxy" refers to the group aryl-O— where the aryl group is as defined herein including optionally substituted aryl groups as also defined herein.

"Carboxy" refers to the group —COOH.

"Carboxyalkyl" refers to the group —C(O)O-alkyl where alkyl is as defined herein.

The term "coupling reagent" refers to Michael acceptors and α-halocarbonyl compounds. "Michael acceptors" refers to α,β-unsaturated carbonyl compounds having the general formula (II):

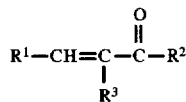

wherein R[1], R[2] and R[3] are as defined herein; or R[1]CH=CR[2]—C(O)XR[8], wherein R[1], R[2], R[8] and X are as defined herein. Such Michael acceptors include, by way of example, α,β-unsaturated aldehydes, α,β-unsaturated ketones, α,β-unsaturated esters, α,β-unsaturated thioesters, α,β-unsaturated amides and the like. "α-Halocarbonyl compounds" refers to compounds having the general formula: W—CHR[1]—C(O)R[2] wherein R[1] and R[2] are as defined herein, and W is chloro, bromo or iodo. Such α-halocarbonyl compounds include, by way of example, α-chloroaldehydes, α-bromoaldehydes, α-iodoaldehydes, α-chloroketones, α-bromoketones, α-iodoketones and the like.

"Cycloalkyl" refers to cyclic alkyl groups or cyclic alkyl rings of from 3 to 8 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like. Examples of suitable cycloalkyl rings include single ring structures such as cyclopentane, cyclohexane, cycloheptane, cyclooctane, and the like, or multiple ring structures such as bicyclo|2.2.1| heptane, bicyclo|3.2.1|octane, and the like. Preferred cycloalkyl rings include cyclopentane, cyclohexane, cycloheptane and bicyclo|3.2.1|octane.

"Cycloalkenyl" refers to cyclic alkenyl groups or cyclic alkenyl rings of from 4 to 8 carbon atoms having a single cyclic ring and at least one point of internal unsaturation which can be optionally substituted with from 1 to 3 alkyl groups. Examples of suitable cycloalkenyl groups include, for instance, cyclobut-2-enyl, cyclopent-3-enyl, cyclooct-3-enyl and the like. Such cycloalkenyl rings include, by way of example, cyclopentene, cyclohexene, and the like.

"Halo" or "halogen" refers to fluoro, chloro, bromo and iodo and preferably is either chloro or bromo.

"Heteroaryl" refers to a monovalent aromatic carbocyclic group of from 2 to 8 carbon atoms and 1 to 4 heteroatoms selected from oxygen, nitrogen and sulfur within the ring.

Unless otherwise constrained by the definition for the heteroaryl substituent, such heteroaryl groups can be optionally substituted with 1 to 3 substituents selected from the group consisting of alkyl, alkoxy, aryl, aryloxy, halo, nitro, heteroaryl, thioalkoxy, thioaryloxy and the like. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heterocycle" or "heterocyclic" refers to a monovalent saturated or unsaturated group having a single ring or multiple condensed rings, from 1 to 8 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 3 substituents selected from the group consisting of alkyl, alkoxy, aryl, aryloxy, halo, nitro, heteroaryl, thioalkoxy, thioaryloxy and the like. Such heteroaryl groups can have a single ring (e.g., pyrrolidnyl, pipridinyl, morpholinyl or tetrahydrofuranyl) or multiple condensed rings (e.g., indolinyl).

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline and the like.

"Thioalkoxyalkyl" refers to the group -alkylene-S-alkyl which includes by way of example, thiomethoxymethyl ($CH_3SCH_2$—), thiomethoxyethyl ($CH_3$—S—$CH_2CH_2$—) and the like.

"Thiol" refers to the group —SH.

"Thioalkoxy" refers to the group —S-alkyl wherein the alkyl group is as defined herein.

"Thioaryloxy" refers to the group aryl-S— wherein the aryl group is as defined herein, including optionally substituted aryl groups as also defined herein.

"Thioheteroaryloxy" refers to the group heteroaryl-S— wherein the heteroaryl group is as defined herein, including optionally substituted heteroaryl groups as also defined herein.

The term "thiosaccharide" refers to a monosaccharide or oligosaccharide having 2 to about 8 saccharide units wherein at least one, and preferably 1 or 2, of the hydroxyl groups of the saccharide is replaced with a thiol group.

The term "thiosaccharide carbonyl compound" refers to a compound having the formula (III):

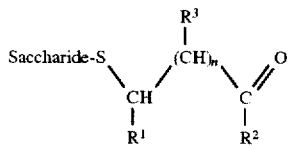

wherein $R^1$, $R^2$, $R^3$, n and saccharide are as defined herein.

The term "substrate" or "solid support" refers to a material having a rigid or semi-rigid surface which contains or can be derivatized to contain reactive functionality which covalently links a compound to the surface thereof. Such materials are well known in the art and include, by way of example, silicon dioxide supports containing reactive Si—OH groups, polyacrylamide supports, polystyrene supports, polyethyleneglycol supports, and the like. Such supports will preferably take the form of small beads, pellets, disks, or other conventional forms, although other forms may be used. In some embodiments, at least one surface of the substrate will be substantially flat.

In one embodiment, the activated ketone compound is covalently attached directly to the solid support or is attached to the support via a linking arm. Linking arms are well known in the art and include, by way of example only, conventional linking arms such as those comprising ester, amide, carbamate, ether, thio ether, urea, amine groups and the like. The linking arm can be cleavable or non-cleavable.

"Cleavable linking arms" refer to linking arms wherein at least one of the covalent bonds of the linking arm which attaches the compound to the solid support can be readily broken by specific chemical reactions thereby providing for compounds comprising activated ketone groups free of the solid support ("soluble compounds"). The chemical reactions employed to break the covalent bond of the linking arm are selected so as to be specific for bond breakage thereby preventing unintended reactions occurring elsewhere on the compound. The cleavable linking arm is selected relative to the synthesis of the compounds to be formed on the solid support so as to prevent premature cleavage of this compound from the solid support as well as not to interfere with any of the procedures employed during compound synthesis on the support. Suitable cleavable linking arms are well known in the art.

"Non-cleavable linking arms" refer to linking arms wherein the covalent bond(s) linking the activated ketone compound to the solid support can only be cleaved under conditions which chemically alters unintended parts of the structure of the compound attached thereto.

The term "substantially homogeneous" refers to collections of molecules wherein at least 80%, preferably at least about 90% and more preferably at least about 95% of the molecules are a single compound or stereoisomers thereof.

The term "stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. The compounds described herein may have one or more asymmetrical carbon atoms and therefore include various stereoisomers. All stereoisomers are included within the scope of the invention.

When chiral centers are found in the thiosaccharide derivatives of this invention, it is to be understood that this invention encompasses all possible stereoisomers. For example, when n is 0 in formula I, the carbon atoms to which $R^1$ and $R^2$ are attached may have an R,R or R,S or S,R or S,S configuration. Similarly, when n is 1, the carbon atoms to which $R^1$, $R^2$ and $R^3$ are attached may have an R,R,R or S,R,R or R,S,R or R,R,S or S,S,R or S,R,S or R,S,S or S,S,S configuration.

The term "removable protecting group" or "protecting group" refers to any group which when bound to a functionality such as hydroxyl, amino, or carboxyl groups prevents reactions from occurring at these functional groups and which protecting group can be removed by conventional chemical or enzymatic steps to reestablish the functional group. The particular removable protecting group employed is not critical.

The terms "heat-labile enterotoxin" or "LT" refer to an enterotoxin of enterotoxigenic *E. coli* which initiates traveller's diarrhea and related conditions. This toxin has a lectin-like activity.

The term "traveller's diarrhea" refers to diarrhea of sudden onset, often accompanied by abdominal cramps, vomiting and fever that occurs sporadically in traveller's, usually during the first week of a trip. This diarrhea is most commonly caused by enterotoxigenic *E. coli*.

The term "cholera" refers to an acute epidemic infectious disease caused by *Vibrio cholerae*, wherein a soluble toxin elaborated in the intestinal tract by the Vibrio alters the permeability of the mucosa, causing a profuse watery diarrhea, extreme loss of fluid and electrolytes, and a state of dehydration and collapse, but no gross morphologic change in the intestinal mucosa.

The terms "cholera toxin" or "CT" refer to an enterotoxin of *V. cholerae* which initiates cholera and related conditions. This toxin has a lectin-like activity.

The phrase "inhibit(s) the binding of heat-labile enterotoxin (LT) and/or cholera toxin (CT) to an LT and/or CT receptor" means that a compound inhibits the binding of LT and/or CT to an LT and/or CT receptor, such as ganglioside $G_{D1b}$ or ganglioside $G_{M1}$, by at least 20% at a concentration of 2 mg/mL under conditions where thiodigalactoside (α-Gal-S-αGal) inhibits binding to the receptor by 20%. Such binding is reported herein as percent toxin activity remaining so that those compounds which result in about 80% or less toxin activity remaining under the bioassay conditions disclosed herein are deemed to inhibit the binding of LT and/or CT to the LT and/or CT receptor.

For purpose of this application, all sugars are referenced using conventional three letter nomenclature. All sugars are assumed to be in the D-form unless otherwise noted, except for fucose, which is in the L-form. Further, all sugars are in the pyranose form.

General Synthetic Procedures

1. Method for Synthesizing Thiosaccharide Derivatives

In one aspect, the methods of this invention involve the novel addition of a thiosaccharide to a coupling reagent selected from the group consisting of Michael reagents and α-halocarbonyl compounds.

Specifically, the thiosaccharide derivatives of this invention are typically prepared by reaction of a suitably protected thiosaccharide intermediate with an α,β-unsaturated carbonyl compound or an α-halocarbonyl compound to provide for a thiosaccharide carbonyl compound. The carbonyl group of the thiosaccharide carbonyl compound is then optionally reduced to provide for a plurality of alcohol and/or amine thiosaccharide derivatives. In one embodiment, the alcohol and/or amine group of the thiosaccharide derivative is further derivatized to provide for a plurality of thiosaccharide derivatives.

The α,β-unsaturated carbonyl compounds employed in preparing the thiosaccharide derivatives of this invention preferably have the general formula (II):

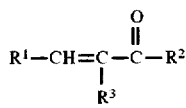

wherein $R^1$, $R^2$ and $R^3$ are as defined above; or $R^1CH=CR^2-C(O)XR^8$, wherein $R^1$, $R^2$, $R^1$ and X are as defined above. These compounds are either commercially available or can be prepared from commercially available materials using art recognized procedures. For example, such compounds can be prepared via a Wittig reaction from an aldehyde, $R^1CHO$, and a β-carbonyl phosphorane, such as $(Ph)_3PC(R^3)C(O)R^2$.

Preferred α,β-unsaturated carbonyl compounds for use in this invention include, by way of example, cyclopent-2-en-1-one, 4,4-dimethylcyclopent-2-en-1-one, cyclohex-2-en-1-one, 4,4-dimethylcyclohex-2-en-1-one, cyclohept-en-1-one, and 3-methylene-2-norbornanone.

The α-halocarbonyl compounds employed in preparing the thiosaccharide derivatives of this invention preferably have the general formula: $W-CHR^1-C(O)R^2$ wherein $R^1$ and $R^2$ are as defined above, and W is chloro, bromo or iodo. Such compounds are either commercially available or can be prepared from commercially available materials using art recognized procedures. Preferred α-halocarbonyl compounds for use in this invention include, by way of example, 2-chlorocyclopentanone and 2-chlorocyclohexanone.

The sugars employed in this invention are any thiol containing saccharides or oligosaccharides wherein the thiol substitution is at any position of the thiosaccharide. For example, thiolactose having a thiol (—SH) group at the 1, 2, 3, 6, 2', 3', 4' or 6' can be used. Methods for chemically modifying saccharides to introduce suitable substitution are well known in the art as illustrated in Ratcliffe, et al.[9] and references cited therein as well as by Defaye[10]. For example, 1-thiosaccharides can be prepared by reacting the saccharide with an acylating agent to convert all of the hydroxyl groups to acyl groups. The 1-acyl group is then selectively converted to the 1-thioacetyl group by reaction with an excess of thiolacetic acid. Hydrolysis then provides for the 1-thiosaccharide.

Alternatively, selective protection of the hydroxyl groups of the saccharide provides for one or more free hydroxyl groups which can be converted into appropriate leaving groups, such as mesyl or halo groups, by conventional chemistry well known in the art. Such leaving groups can then be displaced to afford the corresponding thiol groups. See, for example, International Patent Application Serial No. PCT/CA92/00242. Specifically, a mesyl group is selectively introduced at one of the hydroxyl groups and then reacted with a thioacetyl group (for example potassium thioacetate) to provide for the corresponding thioacetate derivative. Treatment of this compound with a mild base provides for the corresponding thio group.

The resulting thiosaccharide is then reacted with a coupling reagent selected from the group consisting of Michael acceptors and α-halocarbonyl compounds. Typically, this reaction is conducted by contacting the thiosaccharide with at least one equivalent, preferably 1 to 1.2 equivalents, of the coupling reagent in an inert diluent, such as dichloromethane, at a temperature of from about –40° C. to about 50° C. for about 1 to about 6 hours to afford a thiosaccharide carbonyl compound. In a preferred embodiment, when the thiosaccharide reagent is attached to a solid support, the coupling reagent is preferable used in excess to maximize the yield of the resulting thiosaccaride carbonyl compound. Alternatively, when the coupling reagent is attached to a solid support, the thiosaccharide is preferably used in excess relative to the coupling reagent.

The carbonyl group of the thiosaccharide carbonyl compound can then be optionally reduced using a reducing agent to provide for an alcohol derivative. Preferably, this reduction is conducted by contacting the thiosaccharide carbonyl compound with sodium borohydride, preferably about 1.2 to about 2.0 equivalents of sodium borohydride based on the carbonyl compound. Generally, this reaction is conducted in an inert diluent, such as tetrahydrofuran, isopropanol and mixture thereof, at a temperature of about 25° C. to about 30° C. for about 0.5 to about 3.0 hours, to afford the alcohol derivative.

Alternatively, the carbonyl group of the thiosaccharide carbonyl compound can be reductively aminated to provide for an amine derivative. In this reaction, the thiosaccharide carbonyl compound is contacted with an excess of ammonium acetate and at least one equivalent of sodium cyanoborohydride based on the carbonyl compound. This reaction is typically conducted in an inert diluent, such as methanol, tetrahydrofuran and mixtures thereof, at a temperature of about 25° C. to about 30° C. for about 1 to about 72 hours.

The thiosaccharide carbonyl compound can also be reductively aminated in the presence of a primary or secondary amine to provide for amine derivatives. Preferably the amine used in the reductive amination is an amino acid or a derivative thereof, such as amino acid esters. Typically, this reaction is conducted by contacting the thiosaccharide carbonyl compound with a molar excess of an amino acid ester, such as the methyl ester or the tert-butyl ester, preferably with 10 equivalents based on the carbonyl compound, in the presence of at least one molar equivalent, preferably about 1.0 to about 1.2 equivalents, of sodium cyanoborohydride. Typically, this reaction is conducted in an essentially anhydrous inert diluent, such as acetonitrile, at a temperature of about 25° C. to about 30° C. for about 1 to about 72 hours. Subsequently, the ester group of the amino acid can be cleaved using standard conditions to provide the corresponding carboxylic acid.

In a preferred embodiment, the alcohol and/or amine derivatives prepared as described above are further derivatized to form a group selected from esters, amides, carbamates, ureas, thioureas, thioesters and thiocarbamates. Methods for derivatizing alcohols and/or amines to provide for such functional groups are well known to those skilled in the art. For example, alcohols and amines can be reacted with acyl halides to form esters and amides, respectively. Similarly, alcohols and amines can be reacted with isocyanates, among other reagents, to afford carbamates and ureas, respectively. Conditions for such reactions are well recognized in the art.

Figure 2:
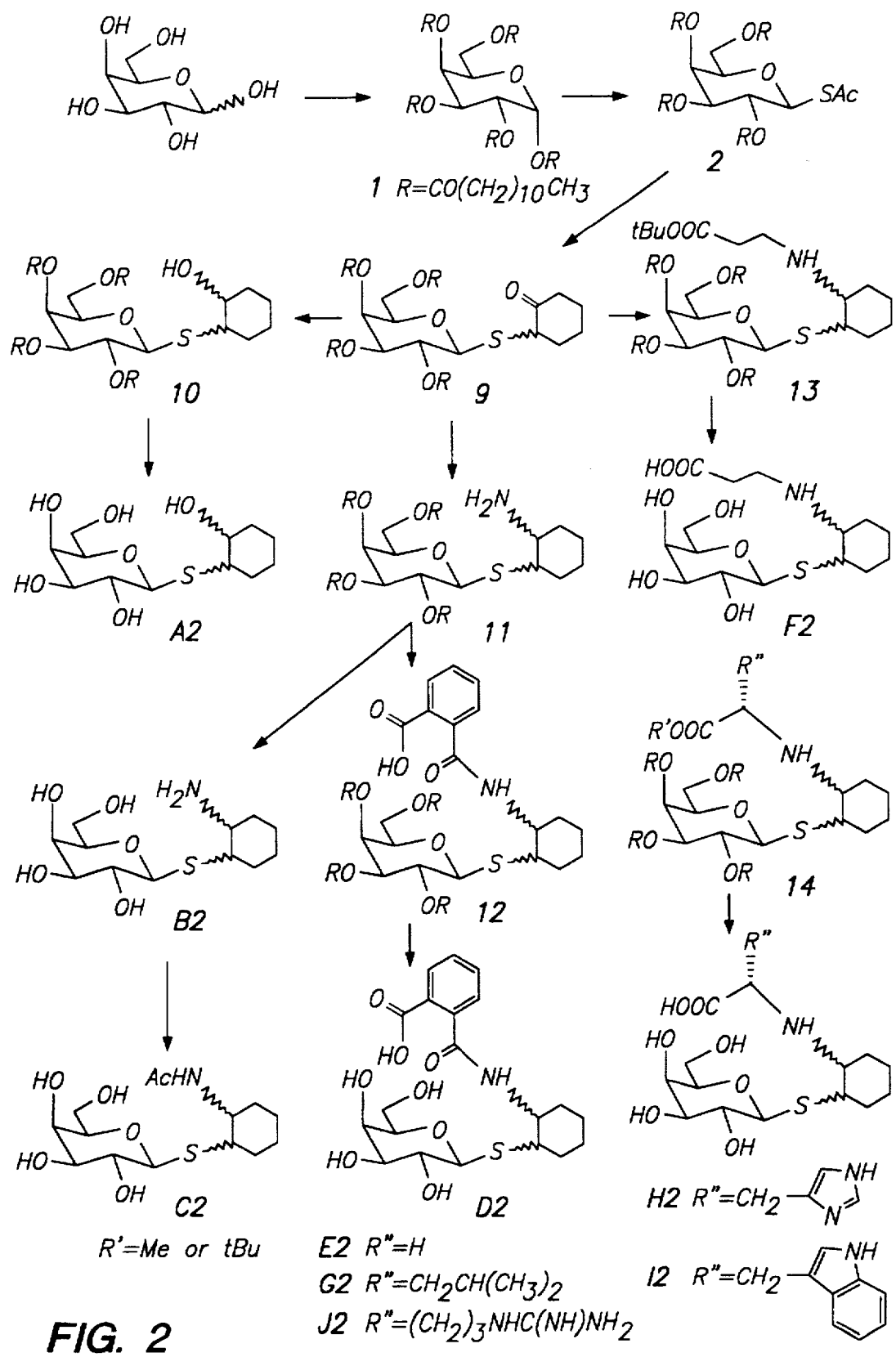
FIG. 2 illustrates a preferred reaction scheme for synthesizing a library of diverse thiosaccharide derivatives using an α-halocarbonyl compound, i.e. 2-chlorocyclohexanone.

Preferred embodiments of this invention are illustrated in FIGS. 1 and 2. FIG. 1 illustrates the synthesis of various 1-thiogalactose derivatives from cyclohept-2-en-1-one. FIG. 2 illustrates the synthesis of various 1-thiogalactose from 2-chlorocyclohexanone. It will be readily apparent to those of ordinary skill in the art that the synthetic procedure illustrated in FIGS. 1 and 2 and following reaction conditions can be modified by selecting the appropriate starting materials and reagents to allow the preparation of a plurality of 1-thiogalactose derivatives.

As shown in FIG. 1, D-galactose is perlauroylated by contacting D-galactose with at least 5 equivalents, and preferably 10 equivalents, of lauroyl chloride. This reaction is generally conducted in an inert diluent, such pentane, hexane, dichloromethane and the like, using a tertiary amine such as pyridine or triethylamine to neutralize the hydrochloric acid generated during the reaction. Preferably, a catalytic amount of 4-(N,N-dimethylamino)pyridine is added to the reaction mixture to facilitate this reaction. Typically, this reaction is conducted at a temperature of from about −78° C. to about 30° C. for about 0.5 to about 96 hours to afford 1,2,3,4,6-penta-O-lauroyl-α-D-galactopyranose, 1, in approximately 70% yield from D-galactose.

Compound 1 is then converted into 1-S-acetyl-2,3,4,6-tetra-O-lauroyl-1-thio-α-D-galactopyranose, 2, by reaction of 1 with an excess of thiolacetic acid. Preferably, this reaction is conducted using about 10 equivalents of thiolacetic acid based on 1. The reaction is generally conducted in the presence of an excess of boron trifluoride etherate, preferably using about 15 to 20 equivalents of boron trifluoride etherate based on 1, in an inert diluent, such as dichloromethane and the like. Typically, this reaction is conducted initially at about 0° C. and then at about 30° C. for about 0.5 to about 48 hours.

Alternatively, compound 2 can be prepared from 1 by contacting 1 with at least one equivalent, preferably 1 to 1.2 equivalents, of benzylamine to selectively remove the 1-lauroyl group. This reaction is typically conducted at about 25° C. to about 30° C. for about 1 to about 96 hours to provide for 2,3,4,6-tetra-O-lauroyl-(α,β)-galactopyranoside. This intermediate is then converted into an O-(2,3,4,6-tetra-O-lauroyl-(α,β)-galactopyranosyl) trichloroacetimidate intermediate by contacting the tetralauroyl compound with an excess of trichloroacetonitrile, preferably about 10 equivalents, and about 0.8 to about 1.0 equivalents, of 1,8-diazabicyclo[5.4.0]undec-7-ene (DBU) in an inert diluent, such as dichloromethane. The resulting O-trichloroacetidate intermediate is then contacted with an excess of thiolacetic acid in an inert diluent, such as dichloromethane, at about 25° C. to about 30° C. for about 1 to about 96 hours to provide for 1-S-acetyl-2,3,4,6-tetra-O-lauroyl-1-thio-α-D-galactopyranose, 2.

The Michael addition of compound 2 to cyclohept-2-en-1-one then affords cycloheptanon-3-yl 2,3,4,6-tetra-O-lauroyl-1-thio-O-D-galactopyranoside, 3. This reaction is typically conducted by contacting 2 with at least one equivalent, preferably 1.0 to 1.2 equivalents, of cyclohep-2-en-1-one in the presence of a molar excess of a dialkylamine, such as diethylamine. Without being limited by any theory, it is believed that the dialkylamine first reacts with the thioacetyl of compound 2 thereby forming in situ the thiol derivative of compound 2 which then reacts under basic conditions generated by the dialkylamine with a Michael adduct.

Typically, this reaction is conducted in an inert diluent, such as dichloromethane, at a temperature of from about −40° C. to about 50° C. for about 1 to about 6 hours.

The carbonyl group of compound 3 can then reduced using a reducing agent to provide for 3-hydroxycycloheptyl 2,3,4,6-tetra-O-lauroyl-1-thio-β-D-galactopyranoside, 4. Preferably, this reduction is conducted by contacting 3 with sodium borohydride, preferably about 1.2 to about 2.0 equivalents of sodium borohydride based on 3. Generally, this reaction is conducted in an inert diluent, such as tetrahydrofuran, isopropanol and mixture thereof, at a temperature of about 25° C. to about 30° C. for about 0.5 to about 3.0 hours. The resulting alcohol, 4, is readily purified by solid-phase extraction on C18 silica gel using pentane as an eluent.

Removal of the lauroyl groups from alcohol 4 is then accomplished by treating 4 with an excess of sodium methoxide in methanol and an inert diluent, such as dichloromethane, at about 25° C. to about 30° C. for about 1 to about 24 hours. Neutralization of the reaction mixture with Amberlite IR-50S (H$^+$) resin then provides for 3-hydroxycycloheptyl 1-thio-β-galactopyranoside, A5.

Alternatively, compound 3 can be reductively aminated to provide for 3-aminocycloheptyl 2,3,4,6-tetra-O-lauroyl-1-thio-β-D-galactopyranoside, 5. In this reaction, compound 3 is contacted with an excess of ammonium acetate and at least one equivalent of sodium cyanoborohydride based on 3. This reaction is typically conducted in an inert diluent, such as methanol, tetrahydrofuran and mixtures thereof, at a temperature of about 25° C. to about 30° C. for about 1 to about 72 hours. The resulting amine compound 5 is readily purified by solid-phase extraction on C18 silica gel using pentane as an eluent.

Optionally, the amine group formed by reductive amination can be acylated with conventional acylating agents under conventional conditions. The acylating agent is generally of the formula L—C(O)R$^6$ where L is a leaving group such as a halide, an activated ester, and the like.

The lauroyl groups are removed from compound 5 by contacting 5 with an excess of sodium methoxide in methanol and an inert diluent, such as dichloromethane, at about 25° C. to about 30° C. for about 1 to about 24 hours. Neutralization of the reaction mixture with Amberlite IR-50S (H$^+$) resin then provides for 3-aminocycloheptyl 1-thio-β-galactopyranoside, B5.

In one example, the primary amine group of compound B5 can optionally be acylated by contacting B5 with an excess of acetic anhydride in methanol containing a trace of water. Generally, this reaction is conducted at about 25° C. to about 30° C. for about 2 to about 24 hours to provide for 3-acetamidocycloheptyl 1-thio-β-galactopyranoside, C5.

Alternatively, the primary amine group of 5 can be acylated with phthalic anhydride before removal of the lauroyl groups to provide for 3-(2-carboxybenzamido) cycloheptyl 2,3,4,6-tetra-O-lauroyl-1-thio-β-D-galactopyranoside, 6. This reaction is typically conducted by contacting compound 5 with at least one molar equivalent, preferably with an excess of phthalic anhydride. Preferably, this reaction is conducted in dry pyridine containing a catalytic amount of 4-(N,N-dimethylamino)pyridine. The reaction is typically conducted at about 25° C. to about 30° C. for about 12 to about 48 hours to provide for compound, 6. Removal of the lauroyl groups from 6 is then accomplished by treating 6 with sodium methoxide in methanol and an inert diluent, such as dichloromethane, at about 25° C. to about 30° C. for about 1 to about 24 hours. Neutralization of the reaction mixture with Amberlite IR-50S (H$^+$) resin then provides for 3-(2-carboxybenzamido)cycloheptyl 1-thio-β-D-galactopyranoside, D5.

As shown in FIG. 1, compound 3 can also be reductively aminated with an amino acid ester to provide for intermediates 7 or 8. Specifically, compound 3 is contacted with a molar excess of β-alanine tert-butyl ester, preferably with 10 equivalents based on 3, in the presence of at least one molar equivalent, preferably about 1.0 to about 1.2 equivalents, of sodium cyanoborohydride. Typically, this reaction is conducted in an essentially anhydrous inert diluent, such as acetonitrile, at a temperature of about 25° C. to about 30° C. for about 1 to about 72 hours. The resulting intermediate 7 is readily purified by solid-phase extraction on C18 silica gel using pentane as the eluent.

The tert-butyl ester group of compound 7 is readily hydrolyzed to the corresponding carboxylic acid by treating 7 with an excess of trifluoroacetic acid in an inert diluent such as dichloromethane. This reaction is typically conducted at about 25° C. to about 30° C. for about 1 to about 10 hours. The lauroyl groups of the resulting carboxylic acid intermediate are then removed using sodium methoxide in methanol as described above to provide for $N^\beta$-|1-(1-thio-$\beta$-D-galactopyranosyl)cyclohept-3-yl|-$\beta$-alanine, F5.

In a similar manner, compound 3 can be reductively aminated using other amino acid esters, such as glycine tert-butyl ester, L-leucine tert-butyl ester, L-histidine methyl ester, L-tryptophan methyl ester, and L-arginine methyl ester, to provide for intermediate 8. In those cases where the amino acid ester employed is a tert-butyl ester, the tert-butyl ester is cleaved as described above using trifluoroacetic acid to afford $N^\alpha$-|1-(1-thio-$\beta$-D-galactopyranosyl)cyclohept-3-yl|-glycine, E5, and $N^\alpha$-|1-(1-thio-$\beta$-D-galactopyranosyl)cyclohept-3-yl|-L-leucine, G5. Alternatively, in those cases where an amino acid methyl ester is employed, the lauroyl groups of intermediate 8 are preferably removed before cleaving the methyl ester by treatment of 8 with sodium methoxide in methanol as described above. Subsequently, the methyl ester of the amino acid moiety is cleaved to the corresponding carboxylic acid by treatment with an excess of aqueous lithium hydroxide for about 0.5 to about 2 hours. Neutralization of the reaction mixture with Amberlite IR-50S (H$^+$) resin then provides for $N^\alpha$-|1-(1-thio-$\beta$-D-galactopyranosyl)cyclohept-3-yl|-L-histidine, H5, $N^\alpha$-|1-(1-thio-$\beta$-D-galactopyranosyl)cyclohept-3-yl|-L-tryptophan, 15, and $N^\alpha$-|1-(1-thio-$\beta$-D-galactopyranosyl)cyclohept-3-yl|-L-arginine, J5.

As noted above, FIG. 2 illustrates the synthesis of various 1-thiogalactose derivatives using an $\alpha$-halocarbonyl carbonyl compound, i.e., 2-chlorocyclohexanone. As shown in FIG. 2, 1-S-acetyl-2,3,4,6-tetra-O-lauroyl-1-thio-$\alpha$-D-galactopyranose, 2, prepared as described above, reacts with 2-chlorocyclohexanone to give cyclohexanon-2-yl 2,3,4,6-tetra-O-lauroyl-1-thio-$\beta$-D-galactopyranoside, 9. This reaction is typically conducted by contacting 2 with at least one equivalent, preferably 1.0 to 1.2 equivalents, of 2-chlorocyclohexanone in the presence of an excess of a dialkylamine, such as diethylamine. Typically, this reaction is conducted in an inert diluent, such as dichloromethane, at a temperature of from about −40° C. to about 50° C. for about 1 to about 6 hours to afford compound 9.

Compound 9 can then be reacted using the same reagents and conditions described above for compound 3 to afford various 1-thiogalactose derivatives. Specifically, compound 9 is reduced with sodium borohydride to provide 10 which, after removal of the lauroyl groups, affords 2-hydroxycyclohexyl 1-thio-$\beta$-D-galactopyranoside, A2.

Alternatively, compound 9 is reductively aminated with ammonium acetate and sodium cyanoborohydride to provide for intermediate 11 which, upon removal of the lauroyl groups, affords 2-aminocyclohexyl 1-thio-$\beta$-D-galactopyranoside, B2. Compound B2 can then be acylated with acetic anhydride to give 2-acetamidocyclohexyl 1-thio-$\beta$-D-galactopyranoside, C2. Alternatively, intermediate 11 can be acylated with phthalic anhydride to provide for intermediate 12 which affords 2-(2-carboxybenzamidocyclohexyl 1-thio-$\beta$-D-galactopyranoside, D2, by removal of the lauroyl groups using the conditions described above.

Additionally, compound 9 can be reductively aminated using an $\beta$-alanine tert-butyl ester to provide for intermediate 13 which then affords $N^\beta$-|1-(1-thio-$\beta$-D-galactopyranosyl)cyclohex-2-yl|-$\beta$-alanine, F2, upon deprotection. Alternatively, compound 9 can be reductive aminated with other amino acid ester, such as glycine tert-butyl ester, L-leucine tert-butyl ester, L-histidine methyl ester, L-tryptophan methyl ester, and L-arginine methyl ester, to provide intermediate 14 which upon deprotection, affords $N^\alpha$-|1-(1-thio-$\beta$-D-galactopyranosyl)cyclohex-2-yl|-glycine E2, $N^\alpha$-|1-(1-thio-$\beta$-D-galactopyranosyl)cyclohex-2-yl|-L-leucine G2, $N^\alpha$-|1-(1-thio-$\beta$-D-galactopyranosyl)cyclohex-2-yl|-L-histidine H2, $N^\alpha$-|1-(1-thio-$\beta$-D-galactopyranosyl)cyclohex-2-yl|-L-tryptophan I2, and $N^\alpha$-|1-(1-thio-$\beta$-D-galactopyranosyl)cyclohex-2-yl|-L-arginine J2.

The methods illustrated in FIGS. 1 and 2 were conducted in a solution phase. Surprisingly, these methods can also be conducted on the solid phase using reaction conditions similar to those described above for the solution phase. When conducted on the solid phase, one of the reagents employed is attached to a solid support via a cleavable or non-cleavable linking arm. Such linking arms are well known in the art as well as their attachment to either the thiosaccharide or the coupling reagent.

Either of the reagents can be attached to the solid support without criticality provided that the attachment does not alter the reactivity of the reagent. For example, a linking arm may be covalently attached to any position of the thiosaccharide other than the thiol group. Such attachments are preferably made through, for example, an ester or ether linkage to one the hydroxyl group of the thiosaccharide. A preferred linking arm is derived from succinic acid.

Similarly, a linking arm can be covalently attached to any position of the coupling reagent provided that the point of attachment does not interfere with the Michael addition of the thiosaccharide to the $\alpha,\beta$-unsaturated carbonyl group or with the displacement of the halide from the $\alpha$-halocarbonyl compound by the thiosaccharide. Accordingly, the linking arm is preferably attached to the coupling reagent through any one of substituents $R^1$-$R^8$ via a covalent bond. Such linkage can be through, for example, an ester, ether, amine, amide, or urea functional group and the like.

2. Method for Preparing A Thiosaccharide Derivative Library

In another aspect, the methods of this invention provide for a thiosaccharide derivative library. Such libraries are produced by synthesizing on each of a plurality of solid supports a single compound wherein each compound comprises a thiosaccharide derivative.

The thiosaccharide derivative libraries provided by this invention are synthesized by first apportioning solid supports among a plurality of reaction vessels. Such supports comprise a reactive functional group capable of covalently binding to the solid support. The functional group is one that is capable of covalently binding a thiosaccharide at a position other than the thiol group. Suitable functional groups include, by way of example, alcohols, amines, isocyanates, carboxylic acid groups, esters and the like. In one embodiment, this is accomplished by selectively blocking the thiol group with a removable blocking group which, after coupling of the thiosaccharide to the solid support, is removed thereby freeing the thiol group for further reaction.

The supports in each reaction vessel are then contacted with a unique thiosaccharide under conditions wherein the thiosaccharide is covalently attached to the solid supports through the reactive functional group. This reaction is typically conducted by contacting the solid support with at least one equivalent, preferably 1 to 5 equivalents, of the thiosaccaride based on the functional groups on the solid support.

After attaching the thiosaccharide to the solid support, the supports are then pooled and the pooled supports are then apportioned among a plurality of reaction vessels.

The supports having a thiosaccharide covalently attached thereto are then contacted in each reaction vessel with a unique coupling reagent selected from the group consisting of Michael acceptors and α-halocarbonyl compounds to provide for a thiosaccharide carbonyl compound which covalently bound to the support. This reaction is preferably conducted as described above.

The thiosaccharide carbonyl compound is then reduced as described above to provide for an alcohol and/or an amine derivative. Optionally, the hydroxy or amino group of these compounds can be further derivatized as described above to form a group selected from esters, amides, carbamates, ureas, thioesters and thiocarbamates.

In an alternative embodiment, the thiosaccharide derivative libraries provide by this invention are synthesized by first apportioning solid supports among a plurality of reaction vessels wherein such supports comprise a reactive functional group covalently bound to the solid support such that the functional group one that is capable of covalently binding a coupling reagent. Such functional groups include, by way of example, alcohols, amines, isocyanates, carboxylic acid groups, esters and the like. The supports in each reaction vessel is then contacted with a unique coupling reagent selected from the group consisting of Michael acceptors and α-halocarbonyl compounds under conditions wherein the coupling reagent is covalently attached to the solid supports through the reactive functional group. Typically, this reaction is conducted by contacting the solid support with at least one equivalent of the coupling reagent, preferably with about 1 to about 5 equivalents, based on the functional groups on the solid support.

After attaching the coupling reagent to the solid support, the supports are then pooled and the pooled supports are then apportioned among a plurality of reaction vessels.

The supports having a coupling reagent covalently attached thereto are then contacted in each reaction vessel with a unique thiosaccharide to provide for a thiosaccharide carbonyl compound which is covalently bound to the support. This reaction is preferably conducted as described above. The thiosaccharide carbonyl compounds can then be reduced to provide for a plurality of alcohol and/or amine derivatives. As above, these alcohol and/or amine derivatives can optionally be further derivatized to provide for a group selected from esters, amides, carbamates, ureas, thioesters, and thiocarbamates.

In a preferred embodiment, an identifier tag is employed in the methods of this invention. The identifier tag has a recognizable feature that is, for example, microscopically or otherwise distinguishable in shape, size, mass, charge, or color. This recognizable feature may arise from the optical, chemical, electronic, or magnetic properties of the tag, or from some combination of such properties. In essence, the tag serves to label a molecule and to encode information decipherable at the level of one (or a few) molecules or solid supports. By using identifier tags to track the synthesis pathway that each member of a chemical library has taken, one can deduce the structure of any chemical in the library by reading the identifier tag.

The identifier tags identify each reagent or other reaction step that an individual library member or solid support has experienced and record the step in the synthesis series in which each reagent was added or other chemical reaction performed. The tags may be attached immediately before, during, or after the reagent addition or other reaction, as convenient and compatible with the type of identifier tag, modes of attachment, and chemistry of activated ketone or other molecular synthesis. The identifier tag can be associated with the thiosaccaride derivatives through a variety of mechanisms, either directly, through a linking molecule, or through a solid support upon which the thiosaccharide derivative is synthesized. In the latter mode, one could also attach the tag to another solid support that, in turn, is bound to the solid support upon which the thiosaccharide derivative is synthesized. The identifier tag is added when the solid supports that have undergone a specific reagent addition or other chemical reaction step are physically together and so can be tagged as a group, i.e., prior to the next pooling step. Preferred identifier tags include, by way of example, peptides[11,12] oligonucleotides[13] and halocarbon derivatives[14].

3. Screening of Thiosaccharide Derivative Libraries

The libraries of thiosaccharide derivatives (e.g., compounds of formula I) may be screened for biological activity. Generally the library to be screen is exposed to a biological substance, usually a protein such as a receptor, enzyme, membrane binding protein or antibody, and the presence or absence of an interaction between the thiosaccharide derivative and the biological substance is determined. Typically this will comprise determining whether the biological substance is bound to one or more of the members of the library. Such binding may be determined by attaching a label to the biological substance. Commonly used labels include fluorescent labels. Other methods of labeling may be used, such as radioactive labels. The degree of binding affinity may be determined by quantitating the amount or intensity of the bound label. Thus, various lead compounds may be selected by identifying which compounds bind the particular biological substance most effectively.

In a preferred embodiment, bead-based libraries are screened by assays in which each different molecule in the library is assayed for its ability to bind to a receptor of interest. The receptor is contacted with the library of thiosaccharide derivatives, forming a bound member between the receptor and any thiosaccharide derivative in the library able to bind the receptor under the assay conditions. The bound thiosaccharide derivative is then identified by examination of the tag associated with that thiosaccharide derivative. The receptor to which the library is exposed under binding conditions can be a mixture of receptors, each of which is associated with an identifier tag specifying the receptor type, and consequently two tags are examined after the binding assay. Specific beads can be isolated in a receptor screening by a number of means, including infinite dilution, micromanipulation, or preferably, flow cytometry (e.g., fluorescence activated cell sorting (FACS)). By adopting cell-sized solid supports or beads, one can use flow cytometry for high sensitivity receptor binding analysis and facile bead manipulation.

Thiosaccharide derivatives can be synthesized on beads and cleaved prior to assay. Cleavage of the thiosaccharide derivatives from the beads may be accomplished cleavable linker arms which are cleaved using conventional methods. In either event, the thiosaccharide derivatives of interest are cleaved from the beads but remain contained within the compartment along with the bead and the identifier tag(s).

Soluble tagged thiosaccharide derivatives can also be screened using an immobilized receptor. After contacting the tagged thiosaccaride derivatives with the immobilized receptor and washing away non-specifically bound molecules, bound, tagged thiosaccharide derivatives are released from the receptor by any of a wide variety of methods. The tags are optionally amplified and then examined and decoded to identify the structure of the molecules that bind specifically to the receptor. A tagged thiosaccharide derivative in solution can be assayed using a receptor immobilized by attachment to a bead, for example, by a competition assay with a fluorescently labeled ligand. One may recover the beads bearing immobilized receptors and sort the beads using FACS to identify positives (diminished fluorescence caused by the library molecule competing with the labeled ligand). The associated identifier tag is then amplified and decoded.

Preferably, the libraries described herein will contain at least about 2 compounds, more preferably at least about $10^2$ compounds, still more preferably from about $10^2$ to about $10^{10}$ compounds and even still more preferably from about $10^3$ to about $10^6$ compounds.

Of particular interest is the identification of thiosaccharide derivatives which block binding of heat labile toxin and/or chlorea toxin to cell surface receptors either in vitro or in vivo, and/or compounds which inhibit binding of enterovirulent microorganisms (e.g., bacteria, virus, fungi, and the like) such as *Vibrio cholerae* and enterotoxigenic strains of *Escherichia coli*.

The following synthetic and biological examples are offered to illustrate this invention and are not to be construed in any way as limiting the scope of this invention. Unless otherwise stated, all temperatures are in degrees Celsius.

The following examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.
Å=angstroms
bd=broad doublet
bs=broad singlet
d=doublet
dd=doublet of doublets
DMAP=dimethylaminopyridine
eq.=equivalents
g=grams
L=liter
m=multiplet
meq=milliequivalent
mg=milligram
mL=milliliter
mmol=millimol
N=normal
q=quartet
quint.=quintet
s=singlet
t=triplet
TFA=trifluoroacetic acid
THF=tetrahydrofuran
TLC=thin layer chromatography
μL=microliter $^1$H-Nmr spectra were recorded with a Brueker AM-360 spectrometer and MALDI-TOF mass spectra were recorded with a HP G2020A (LD-TOF) instrument. Optical rotations were measured with a Perkin-Elmer 241 polarimeter. Reactions were monitored by TLC on Silica Gel FG254 (E. Merck, Darmstadt, Germany).

Example A

Solid-Phase Extraction of Lauroylated Intermediates

As indicated in the following examples, certain lauroylated reaction intermediates were purified by solid-phase extraction. In this purification procedure, the reaction mixture is concentrated, re-dissolved in methanol, and applied onto C18 silica (Waters Prep C18, 125 Å, 1 g per 20 mg lauroylated carbohydrate). The C18 silica is then washed with methanol (10 mL/g C18 silica) and the product is eluted with pentane (10 mL/g C18 silica). For L-arginine containing compounds, the reaction mixture is concentrated, re-dissolved in 70% methanol and applied onto C18 silica. The C18 silica is then washed with 70% methanol and the product is eluted with methanol. The resulting product contains no residual reagents as determined by TLC, $^1$H-nmr, or MALDI-TOF mass spectroscopy.

Example B 1 2,3,4,6-Penta-O-lauroyl-α-D-galactopyranose 1

To a suspension of galactose (3.78 g, 21.0 mmol), pyridine (50 mL), and 4-dimethylaminopyridine (cat.) in pentane (150 mL) under argon atmosphere, was added lauroyl chloride (50 mL, 210 mmol) at −78° C. The mixture was allowed to reach ambient temperature. The resulting white slurry slowly dissolved and a fine precipitate of pyridinium hydrochloride formed. After 40 h, the pyridinium hydrochloride was filtered off and the pentane solution was concentrated. Column chromatography (SiO$_2$, pentane/EtOAc 9:1) gave 1 (16.0 g, 70% yield), $[\alpha]_D^{25}$+39° (c 0.9, CHCl$_3$). $^1$H-Nmr data (CHCl$_3$): δ 6.39 (d, 1H, J 2.4 Hz, H-1), 5.51 (br s, 1H, H-4), 5.35 (m, 2H, H-2 and H-3), 4.32 (br t, 1H, J 6.6 Hz, H-5), 4.08 (d, 2H, J 6.6 Hz, H-6a and H-6b), 2.39, 2.38, 2.30, 2.26 (4 t, 2H each, J 7.5 Hz, —CH$_2$CO—), 2.21 (m, 2H, —CH$_2$CO—), 0.88 (t, 15 H, J 7.0 Hz, —CH3). Anal. Calcd for C$_{66}$H$_{122}$O$_{11}$: C, 72.2; H, 11.3. Found: C, 72.6; H, 11.5.

Example C

1-S-Acetyl-2,3,4,6-tetra-O-lauroyl-1-thio-a-D-galactopyranose 2

Method 1: To compound 1 (from Example B, 1 g, 0.91 mmol) and thioacetic acid (0.4 mL, 9.1 mmol) in dry dichloromethane (5 mL) under argon at 0° C., was added boron trifluoride etherate (1.7 mL, 13.6 mmol). The coldbath was removed after 10 min and after 24 h the mixture was diluted with dichloromethane, washed with saturated sodium bicarbonate, dried over sodium sulfate, and concentrated. Column chromatography (SiO$_2$, pentane/Et2O/EtOAc 9:1:1) gave 2 (0.60 g, 70% yield).

Method 2: To compound 1 (from Example B, 276.5 mg, 0.253 mmol) in dry tetrahydrofuran (2.0 mL) under argon, was added benzylamine (27.9 μL, 0.255 mmol). The mixture was concentrated after 70 h. The residue was dissolved in dry dichloromethane (4.0 mL) under argon and then trichloroacetonitrile (250 μL, 2.5 mmol) and 1,8-diazabicyclo [5.4.0]undec-7-ene (30 μL, 0.2 mmol) were added. The mixture was concentrated after 3 h and the residue was flashed through a short column (SiO$_2$, pentane/EtOAc 19:1), then concentrated. To the residue in dry dichloromethane (3.5 mL) under argon, was added thiolacetic acid (1 mL). After 96 h, the reaction mixture was concentrated and the residue was purified by column chromatography (SiO$_2$, pentane, EtOAc 19:1) to give 2 (90 mg, 37% yield), $|\alpha|_D^{25}$ 21° (c 1, CHCl$_3$). $^1$H-Nmr data (CHCl$_3$): δ 5.47 (d, 1H, J 3.4 Hz, H-4), 5.32 (t, 1H, J 10.0 Hz, H-2), 5.25 (d, 1H, J 10.0 Hz, H-1), 5.12 (dd, 1H, J 3.4 and 10.0 Hz, H-3), 4.08 (m, 3H, H-5, H-6a and H-6b), 2.14–2.43 (m, 8H, —CH$_2$CO—), 2.37 (s, 3H, —SAc), 0.88 (t, 15 H, J 7.0 Hz, —CH3). Anal. Calcd for C$_{56}$H$_{102}$O$_{10}$S: C, 69.5; H, 10.6; S, 3.3. Found: C, 69.4; H, 10.8; S, 3.5.

Example D

General Procedure for Michael Additions and α-Halocarbonyl Substitutions

To compound 2 (1 mmol) and an electrophile (1.2 mmol) in dry dichloromethane (8 mL) under argon, was added Et$_2$NH (4 mL). After 1–3 h, the mixture was concentrated and the residue was purified by column chromatography on SiO$_2$ by eluting with pentane/EtOAc. The products were characterized with $^1$H-nmr spectroscopy and MALDI-TOF mass spectroscopy.

Example E

General Procedure for Reduction to Alcohols

To the product from Example D (100 μmol) in dry tetrahydrofuran (2.0 mL) and isopropanol (0.7 mL) under argon atmosphere, was added NaBH$_4$ (150 μmol). After 0.5–3 h, the mixture was concentrated and the residue was purified according to the solid-phase extraction procedure of Example A. The product alcohols were characterized with $^1$H-nmr spectroscopy and MALDI-TOF mass spectroscopy.

Example F

General Procedure for Reductive Amination to a Primary Amine

To the product from Example D (100 μmol) and ammonium acetate (75 mg, 1 mmol) in dry methanol (2.3 mL) and tetrahydrofuran (0.9 mL) under argon, was added NaCNBH$_3$ (100 μmol). After 1–72 h, the mixture was concentrated and the residue purified according to the solid-phase extraction procedure of Example A. The product amines were characterized with $^1$H-nmr spectroscopy and MALDI-TOF mass spectroscopy.

Example G

General Procedure for Acylation of Primary Amines with Phthalic Anhydride

The O-lauroylated primary amine from Example F (100 μmol), phthalic anhydride (2.7 mmol), and 4-(N,N-dimethylamino)pyridine (catalytic) were dissolved in dry pyridine. The mixture was concentrated after 12–48 h and the residue purified according to the solid-phase extraction procedure of Example A. The product 2-carboxybenzamides were characterized with $^1$H-nmr spectroscopy and MALDI-TOF mass spectroscopy.

Example H

General Procedure for Reductive Amination with Amino Acids

To the product from Example D (100 μmol) and an amino acid tert-butyl ester hydrochloride or methyl ester hydrochloride (1 mmol) in dry MeCN (2.25 mL) and THF (0.75 mL), was added NaCNBH$_3$ (100 μmol). After 1–72 h, the mixture was concentrated and the residue was purified according to the solid-phase extraction procedure of Example A. The product N-alkylated amino acids were characterized with $^1$H-nmr spectroscopy and MALDI-TOF mass spectroscopy.

Example I

General Procedure for Deblocking of Alcohols

To the lauroylated alcohol from Example E (100 μmol) in dry methanol (7.1 mL) and dichloromethane (1.4 mL) under argon atmosphere, was added methanolic sodium methoxide (1M, 50 μL). After 1–24 h, the mixture was neutralized with Amberlite IR-50S (H$^+$) resin, filtered and concentrated. The residue was dissolved in water and applied onto a column of C18 silica (Waters Prep C18, 125 Å, 5 g). The C18 silica was washed with water (50 mL), and the product was then eluted with 70% methanol (50 mL). The resulting alcohols were characterized with $^1$H-nmr spectroscopy and MALDI-TOF mass spectroscopy.

Example J

General Procedure for Deblocking of Primary Amines

To the O-lauroylated primary amine from Example F (100 μmol) in dry methanol (7.1 mL) and dichloromethane (1.4 mL) under argon, was added methanolic sodium methoxide (1M, 50 μL). After 1–24 h, the mixture was neutralized with Amberlite IR-50S (H$^+$) resin, filtered and concentrated. The residue was dissolved in dichloromethane/methanol 2:1 and applied to a Waters SepPak Plus Longbody SiO$_2$ cartridge. The cartridge was washed with dichloromethane/methanol (2:1) and then the product was eluted with dichloromethane/methanol/water (5:5:1) (20 mL) and concentrated. The residue was dissolved in water and applied onto a column of C18 silica (Waters Prep C18, 125 Å, 5 g). The C18 silica was washed with water (50 mL) and then the product was eluted with methanol (50 mL). The resulting primary amines were characterized with 1H-nmr spectroscopy and MALDI-TOF mass spectroscopy.

Example K

General Procedure for N-Acetylation of Primary Amines

To the primary amine from Example J (100 μmol) in moist methanol (4.4 mL) was added acetic anhydride (0.4 mL). The mixture was concentrated after 2–24 h, re-dissolved in water and applied to a column of C18 silica (Waters Prep C18, 125 Å, 5 g). The C18 silica was washed with water (50 mL) and then the product was eluted with methanol (50 mL). The resulting acetamides were characterized with $^1$H-nmr spectroscopy and MALDI-TOF mass spectroscopy.

Example L

General Procedure for Deblocking of 2-Carboxybenzamides

To the O-lauroylated 2-carboxybenzamide from Example G (100 μmol) in dry methanol (7.1 mL) and dichloromethane (1.4 mL) under argon, was added methanolic sodium methoxide (1M, 50 μL). After 1–24 h, the mixture was neutralized with Amberlite IR-50S (H$^+$) resin, filtered and concentrated. The residue was dissolved in dichloromethane/methanol (8:1) and applied to a Waters SepPak Plus Longbody SiO₂ cartridge. The cartridge was washed with dichloromethane/methanol (8:1) and then the product was eluted with dichloromethane/methanol/water (65:35:5) (20 mL) and concentrated. The residue was dissolved in water and applied to a column of C18 silica (Waters Prep C18, 125 Å, 5 g). The C18 silica was washed with water (50 mL), and then the product was eluted with methanol (50 mL). The resulting 2-carboxybenzamides were characterized with $^1$H-nmr spectroscopy and MALDI-TOF mass spectroscopy.

Example M

General Procedure for Deblocking of N-Alkylated Glycine, β-Alanine, and L-Leucine Compounds The N-alkylated amino acid tert-butyl ester from Example H (100 μmol) was treated with trifluoroacetic acid (3.5 mL) in dry dichloromethane (3.5 mL) for 1–10 h. n-Propyl acetate (8 mL) and toluene (16 mL) were added and the mixture was concentrated, then co-concentrated twice with toluene. To the residue in dry methanol (7.1 mL) and dichloromethane (1.1 mL) under an argon atmosphere was added methanolic sodium methoxide (1M, 200 μL). After 1–24 h, the mixture was neutralized with Amberlite IR-50S (H⁺) resin, filtered and concentrated. The residue was dissolved in dichloromethane/methanol (9:1) and applied to a Waters SepPak Plus Longbody SiO₂ cartridge. The cartridge was washed with dichloromethane/methanol (9:1) and then the product was eluted with dichloromethane/methanol/water (65:35:5) (20 mL) and concentrated. The residue was dissolved in water and applied to a column of C18 silica (Waters Prep C18, 125 Å, 5 g). The C18 silica was washed with water (50 mL) and then the product was eluted with 70% methanol (50 mL). The resulting N-alkylated glycine, β-alanine, and L-leucine compounds were characterized with $^1$H-nmr spectroscopy and MALDI-TOF mass spectroscopy.

Example N

General Procedure for Deblocking of N-Alkylated L-Histidine and L-Tryptophan Compounds To the N-alkylated amino acid methyl ester from Example H (100 μmol) in dry methanol (7.3 mL) and dichloromethane (1.1 mL) under an argon atmosphere was added methanolic sodium methoxide (1M, 50 μL). After 1–24 h, the mixture was neutralized with Amberlite IR-50S (H⁺) resin, filtered and concentrated. The residue was dissolved in 70% methanol and applied to a column of C18 silica (Waters Prep C18, 125 Å, 5 g) and then the product was eluted with 70% methanol (50 mL). To the residue in water (3.7 mL) was added aqueous lithium hydroxide (1M, 0.3 mL). After 0.5–2 h, the mixture was neutralized with Amberlite IR-50S (H⁺) resin, filtered and concentrated. The residue was dissolved in dichloromethane/methanol (9:1) and applied to a Waters SepPak Plus Longbody SiO² cartridge. The cartridge was washed with dichloromethane/methanol (9:1) and then the product was eluted with dichloromethane/methanol/water (65:35:5) (20 mL) and concentrated. The residue was dissolved in water and applied to a column of C18 silica (Waters Prep C18, 125 Å, 5 g). The C18 silica was washed with water (50 mL), and the product was eluted with 70% methanol (50 mL). The resulting N-alkylated L-histidine and L-tryptophan compounds were characterized with $^1$H-nmr spectroscopy and MALDI-TOF mass spectroscopy.

Example O

General Procedure for Deblocking of N-Alkylated L-Arginine Compounds

To the N-alkylated arginine methyl ester from Example H (100 μmol) in dry methanol (7.3 mL) and dichloromethane (1.1 mL) under an argon atmosphere was added methanolic sodium methoxide (1M, 50 μL). After 1–24 h, the mixture was neutralized with Amberlite IR-50S (H⁺) resin, filtered and concentrated. The residue was dissolved in 70% methanol and applied to a column of C18 silica and then the product was eluted with 70% methanol (50 mL). To the residue in water (3.7 mL) wa then added aqueous lithium hydroxide (1M, 0.3 mL). After 0.5–2 h, the mixture was neutralized with Amberlite IR-50s (H⁺) resin, filtered and concentrated. The residue was dissolved in water and applied to column of C18 silica (Waters Prep C18, 125 Å, 5 g). The C18 silica was washed with water (50 mL) and then the product was eluted with 50% methanol (50 mL). The resulting N-alkylated L-arginine compounds were characterized with $^1$H-nmr spectroscopy and MALDI-TOF mass spectroscopy.

Example 1

Synthesis of 2-Hydroxycyclopentyl 1-Thio-β-D-galactopyranoside A1

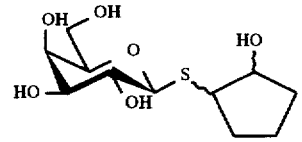

The title compound was prepared according to procedures D, E and I above using 2-chlorocyclopentanone as the electrophile. Mass spectra data was as follows: M (calcd.): 280.34; M (found): 304.9 (M+Na⁺). Selected nmr data was as follows: 1H-nmr (CD₃OD): δ 4.44, 4.43, 4.38, and 4.35 (4 d, J 10 Hz), 2.21, 1.99, 1.82, and 1.64 (4 m).

Example 2

Synthesis of 2-Hydroxycyclohexyl 1-Thio-β-D-galactopyranoside A2

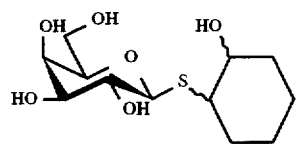

The title compound was prepared according to procedures D, E and I above using 2-chlorocyclohexanone as the electrophile. Mass spectra data was as follows: M (calcd.): 294.34; M (found): 318.8 (M+Na⁺).

Example 3

Synthesis of (2-Hydroxybicyclo[2.2.1]cycloheptyl) methyl 1-Thio-β-D-galactopyranoside A4

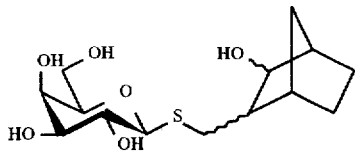

The title compound was prepared according to procedures D, E and I above using 3-methylene-2-norbornanone as the electrophile. Mass spectra data was as follows: M (calcd.): 320.41; M (found): 344.6 (M+Na$^+$). Selected nmr data was as follows: 1H-nmr (CD$_3$OD): δ 4.32 and 4.31 (2 d, J 10 Hz), 3.89 (br d, J 3.5 Hz), 2.88 and 2.85 (2 dd, J 7 and 12 Hz), 2.69 and 2.67 (2 dd, J 10 and 12 Hz.), 2.38 (br s), 2.05 (m), 1.85 (m), 1.58 (m), 1.33 (m).

Example 4

Synthesis of 3-Hydroxycycloheptyl 1-Thio-β-D-galactopyranoside A5

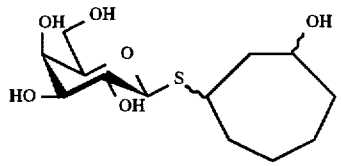

The title compound was prepared according to procedures D, E and I above using cyclohept-en-1-one as the electrophile. Mass spectra data was as follows: M (calcd.): 308.40; M (found): 332.1 (M+Na$^+$).

Example 5

Synthesis of 5,5-Dimethyl-3-hydroxycyclopentyl 1-Thio-β-D-galactopyranoside A6

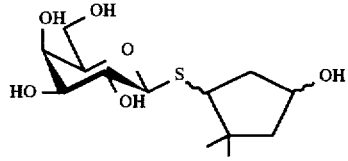

The title compound was prepared according to procedures D, E and I above using 4,4-dimethylcyclopent-2-en-1-one as the electrophile. Mass spectra data was as follows: M (calcd.): 308.40; M (found): 332.1 (M+Na$^+$).

Example 6

Synthesis of 3-Hydroxycyclopentyl 1-Thio-β-D-galactopyranoside A7

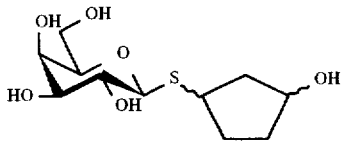

The title compound was prepared according to procedures D, E and I above using cyclopent-en-1-one as the electrophile. Mass spectra data was as follows: M (calcd.): 280.34; M (found): 304.9 (M+Na$^+$).

Example 7

Synthesis of 6,6-Dimethyl-3-hydroxycyclohexyl 1-Thio-β-D-galactopyranoside A9

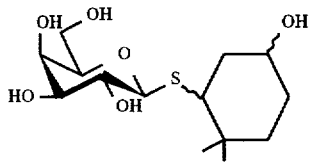

The title compound was prepared according to procedures D, E and I above using 4,4-dimethylcyclohex-2-en-1-one as the electrophile. Mass spectra data was as follows: M (calcd.): 322.42; M (found): 346.6 (M+Na$^+$).

Example 8

Synthesis of 3-Hydroxycyclohexyl 1-Thio-β-D-galactopyranoside A10

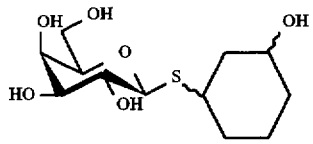

The title compound was prepared according to procedures D, E and I above using cyclohex-2-en-1-one as the electrophile. Mass spectra data was as follows: M (calcd.): 294.37; M (found): 318.3 (M+Na$^+$).

Example 9

Synthesis of 2-Aminocyclopentyl 1-thio-β-D-galactopyranoside B 1

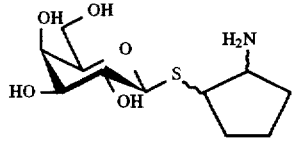

The title compound was prepared according to procedures D, F and J above using 2-chlorocyclopentanone as the electrophile. Mass spectra data was as follows: M (calcd.):

279.36; M (found): n.a. Selected nmr data was as follows: 1H-nmr (CD₃OD): δ 4.48, 4.46, 4.38, and 4.28 (4 d, J 10 Hz), 2.13, 1.75, and 1.59 (3 m).

Example 10

Synthesis of 2-Aminocyclohexyl 1-Thio-β-D-galactopyranoside B2

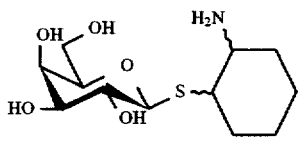

The title compound was prepared according to procedures D, F and J above using 2-chlorocyclohexanone as the electrophile. Mass spectra data was as follows: M (calcd.): 293.38; M (found): 295.8 (M+H⁺), 319.7 (M+Na⁺).

Example 11

Synthesis of (2-Aminobicyclo[2.2.1]cycloheptyl) methyl 1-Thio-β-D-galactopyranoside B4

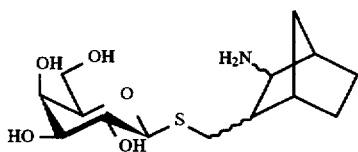

The title compound was prepared according to procedures D, F and J above using 3-methylene-2-norbornanone as the electrophile. Mass spectra data was as follows: M (calcd.): 319.42; M (found): 321.6 (M+H⁺). Selected nmr data was as follows: 1H-nmr (CD₃OD): δ 4.42, 4.41, 4.38, and 4.35 (4 d, J 10 Hz), 2.35 (br s), 2.05 (m), 1.50 (m).

Example 12

Synthesis of 3-Aminocycloheptyl 1-Thio-β-D-galactopyranoside B5

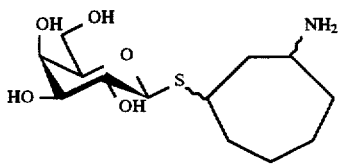

The title compound was prepared according to procedures D, F and J above using cyclohept-2-en-1-one as the electrophile. Mass spectra data was as follows: M (calcd.): 307.41; M (found): 333.0 (M+Na⁺).

Example 13

Synthesis of 5,5-Dimethyl-3-aminocyclopentyl 1-Thio-β-D-galactopyranoside B6

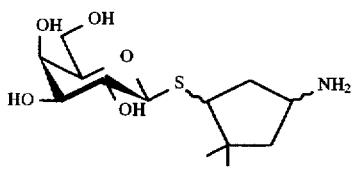

The title compound was prepared according to procedures D, F and J above using 4,4-dimethylcyclopent-2-en-1-one as the electrophile. Mass spectra data was as follows: M (calcd.): 309.35; M (found): n.a. Selected nmr data was as follows: 1H-nmr (CD₃OD): δ 4.33, 4.32, 4.31, and 4.29 (4 d, J 10 Hz), 3.88 and 3.86 (2 br d, J 3.6 Hz), 1.63 (m), 1.15, 1.13, 1.11, 1.09, and 1.08 (5 s).

Example 14

Synthesis of 3-Aminocyclopentyl 1-Thio-β-D-galactopyranoside B7

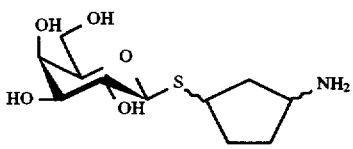

The title compound was prepared according to procedures D, F and J above using cyclopent-2-en-1-one as the electrophile. Mass spectra data was as follows: M (calcd.): 279.35; M (found): n.a. Selected nmr data was as follows: 1H-nmr (CD₃OD): δ 4.46, 4.40, 4.38, and 4.34 (4 d, J 10 Hz), 3.88 (br s), 2.61, 2.27, 2.15, 1.82, and 1.64 (5 m).

Example 15

Synthesis of 3-Aminocyclohexyl 1-Thio-β-D-galactopyranoside B10

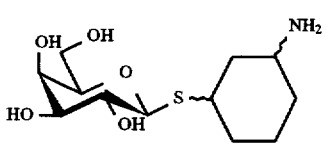

The title compound was prepared according to procedure D, F and J above using cyclohex-2-en-1-one as the electrophile. Mass spectra data was as follows: M (calcd.): 293.38; M (found): 316.2 (M+Na⁺).

Example 16

Synthesis of 2-Acetamidocyclohexyl 1-Thio-β-D-galactopyranoside C2

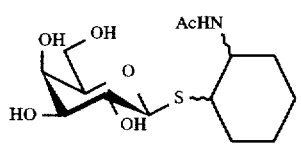

The title compound was prepared according to procedures D, F, J and K above using 2-chlorocyclhexanone as the electrophile. Mass spectra data was as follows: M (calcd.): 335.42; M (found): 359.4 (M+Na$^+$).

Example 17

Synthesis of 3-Acetamidocycloheptyl 1-Thio-β-D-galactopyranoside C5

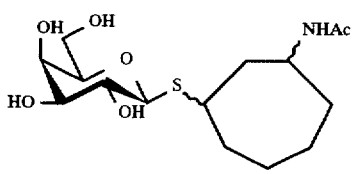

The title compound was prepared according to procedures D, F, J and K above using cyclohept-2-en-1-one as the electrophile. Mass spectra data was as follows: M (calcd.): 349.42; M (found): 372.5 (M+Na$^+$).

Example 18

Synthesis of 3-Acetamidocyclopentyl 1-Thio-β-D-galactopyranoside C7

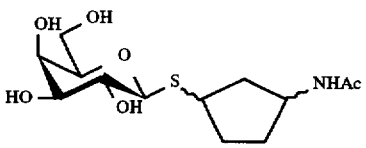

The title compound was prepared according to procedures D, F, J and K above using cyclopent-2-en-1-one as the electrophile. Mass spectra data was as follows: M (calcd.): 321.39; M (found): 349.5 (M+Na$^+$).

Example 19

Synthesis of 3-Acetamidocyclohexyl 1-Thio-β-D-galactopyranoside C10

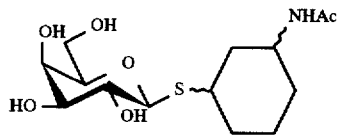

The title compound was prepared according to procedures D, F, J and K above using cyclohex-2-en-1-one as the electrophile. Mass spectra data was as follows: M (calcd.): 335.42; M (found): n.a. Selected nmr data was as follows: 1H-nmr (CD$_3$OD): δ 4.52, 4.46, and 4.45 (3 d, J 10 Hz), 3.90 (d, J 3.6 Hz), 2.96, 2.18, 1.94, 1.78, and 1.23 (5 m), 1.91, 1.92, 1.885, and 1.880 (4s).

Example 20

Synthesis of 2-(2-Carboxybenzamidocyclohexyl 1-Thio-3-D-galactopyranoside D2

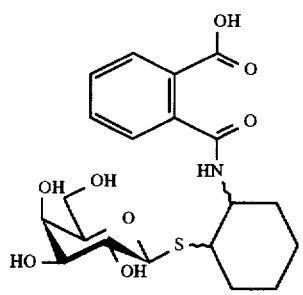

The title compound was prepared according to procedures D, F, G and L above using 2-chlorocyclohexanone as the electrophile. Mass spectra data was as follows: M (calcd.): 439.52; M (found): 465.9 (M+Na$^+$).

Example 21

Synthesis of (2-(Carboxybenzamido)bicyclo[2.2.1] cycloheptyl)methyl 1-Thio-β-D-galactopyranoside D4

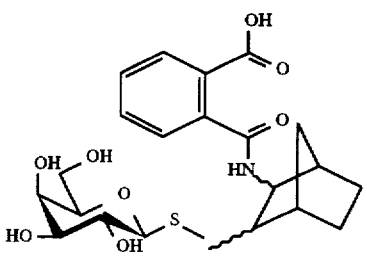

The title compound was prepared according to procedures D, F, G and L above using 3-methylene-2-norbornanone as the electrophile. Mass spectra data was as follows: M (calcd.): 467.54; M (found): 492.4 (M+Na$^+$). Selected nmr data was as follows: 1H-nmr (CD$_3$OD): δ 7.35–7.75 (m), 4.41, 4.35, 4.31, and 4.30 (4 d, J 10 Hz), 3.88 (br s), 2.40 (br s), 1.50 (m).

Example 22

Synthesis of 3-(2-Carboxybenzamido)cycloheptyl 1-Thio-β-D-galactopyranoside D5

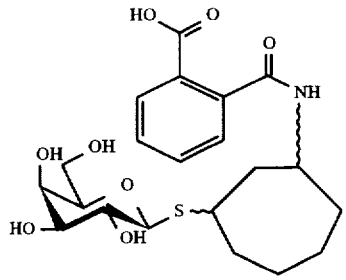

The title compound was prepared according to procedures D, F, G and L above using cyclohept-2-en-1-one as the electrophile. Mass spectra data was as follows: M (calcd.): 453.52; M (found): 479.6 (M+Na⁺).

Example 23

Synthesis of 6,6-Dimethyl-3-(2-Carboxybenzamido)cyclohexyl 1-Thio-β-D-galactopyranoside D9

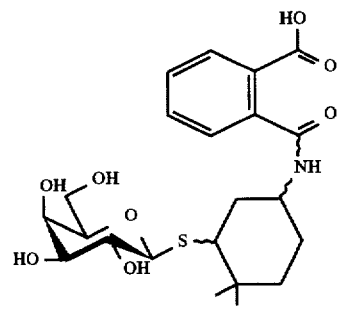

The title compound was prepared according to procedures D, F, G and L above using 4,4-dimethylcyclohex-2-en-1-one as the electrophile. Mass spectra data was as follows: M (calcd.): 469.55, M (found): 492.4 (M+Na⁺).

Example 24

Synthesis of $N^\alpha$-|1-(1-Thio-β-D-galactopyranosyl) cyclopent-2-yl|-glycine E1

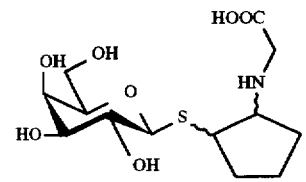

The title compound was prepared according to procedures D, H and M above using 2-chlorocyclopentanone as the electrophile and glycine tert-butyl ester as the amino acid ester. Mass spectra data was as follows: M (calcd.): 337.39; M (found): 363.4 (M+Na⁺).

Example 25

Synthesis of $N^\alpha$-|1-(1-Thio-β-D-galactopyranosyl) cyclohex-2-yl|-glycine E2

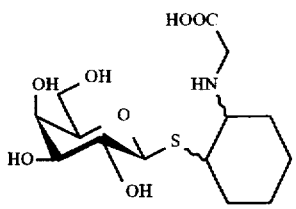

The title compound was prepared according to procedures D, H and M above using 2-chlorocyclohexanone as the electrophile and glycine tert-butyl ester as the amino acid ester. Mass spectra data was as follows: M (calcd.): 351.42; M (found): 353.5 (M+H⁺), 376.5 (M+Na⁺).

Example 26

Synthesis of $N^\alpha$-|1-((1-Thio-β-D-galactopyranosyl)methyl)bicyclo|2.2.1|hept-2-yl|-glycine E4

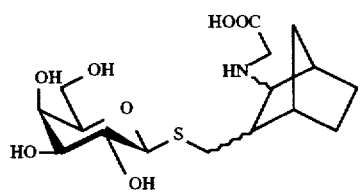

The title compound was prepared according to procedures D, H and M above using 3-methylene-2-norbornanone as the electrophile and glycine tert-butyl ester as the amino acid ester. Mass spectra data was as follows: M (calcd.): 377.46; M (found): 401.4 (M+Na⁺). Selected nmr data was as follows: 1H-nmr (CD₃OD): δ 4.42, 4.40, 4.38, and 4.35 (4 d, J 10 Hz), 2.90 (2 s), 2.60 (br s), 2.42 (m), 1.50 (m).

Example 27

Synthesis of $N^\alpha$-|1-(1-Thio-β-D-galactopyranosyl) cyclohept-3-yl|-glycine E5

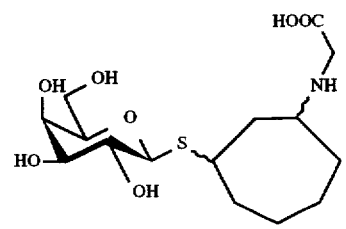

The title compound was prepared according to procedures D, H and M above using cyclohept-2-en-1-one as the electrophile and glycine tert-butyl ester as the amino acid ester. Mass spectra data was as follows: M (calcd.): 365.45; M (found): 367.4 (M+H⁺), 389.9 (M+Na⁺).

Example 28

Synthesis of N$^\alpha$-[1-(1-Thio-β-D-galactopyranosyl)-6,6-dimethylcyclohex-3-yl]-glycine E9

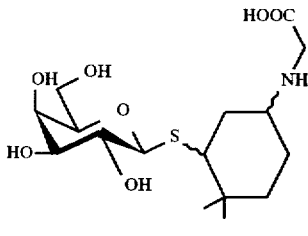

The title compound was prepared according to procedures D, H and M above using 4,4-dimethylcyclohex-2-en-1-one as the electrophile and glycine tert-butyl ester as the amino acid ester. Mass spectra data was as follows: M (calcd.): 379.47; M (found): 380.6 (M+H$^+$), 403.5 (M+Na$^+$).

Example 29

Synthesis of N$^\alpha$-[1-(1-Thio-β-D-galactopyranosyl) cyclohex-3-yl]-glycine E10

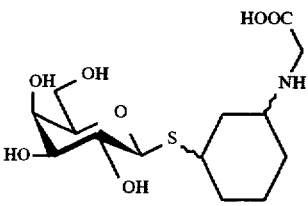

The title compound was prepared according to procedures D, H and M above using cyclohex-2-en-1-one as the electrophile and glycine tert-butyl ester as the amino acid ester. Mass spectra data was as follows: M (calcd.): 351.42; M (found): 375.5 (M+Na$^+$).

Example 30

Synthesis of N$^\beta$-[1-(1-Thio-β-D-galactopyranosyl) cyclopent-2-yl]-β-alanine F1

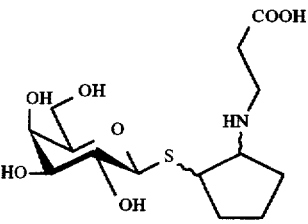

The title compound was prepared according to procedures D, H and M above using 2-chlorocyclopentanone as the electrophile and β-alanine tert-butyl ester as the amino acid ester. Mass spectra data was as follows: M (calcd.): 351.42; M (found): 353.3 (M+H$^+$), 375.5 (M+Na$^+$), 398.3 (M+K$^+$).

Example 31

Synthesis of N$^\beta$-[1-(1-Thio-β-D-galactopyranosyl) cyclohex-2-yl]-β-alanine F2

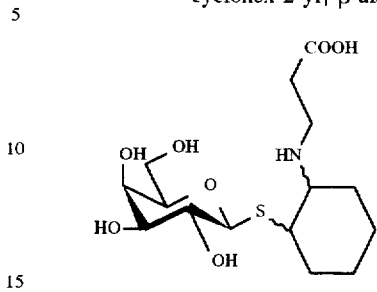

The title compound was prepared according to procedures D, H and M above using 2-chlorocyclohexanone as the electrophile and β-alanine tert-butyl ester as the amino acid ester. Mass spectra data was as follows: M (calcd.): 365.45; M (found): 367.4 (M+H$^+$), 389.9 (M+Na$^+$), 412.0 (M+K$^+$).

Example 32

Synthesis of N$^\beta$-[1-(1-Thio-β-D-galactopyranosyl) cyclohept-3-yl]-β-alanine F5

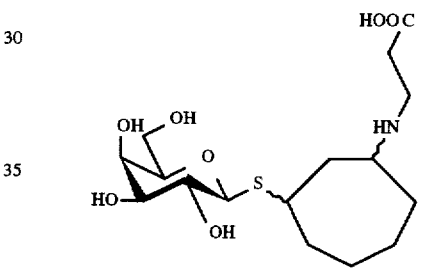

The title compound was prepared according to procedures D, H and M above using cyclohept-2-en-1-one as the electrophile and β-alanine tert-butyl ester as the amino acid ester. Mass spectra data was as follows: M (calcd.): 379.45; M (found): 381.7 (M+H$^+$), 403.5 (M+Na$^+$), 426.0 (M+K$^+$).

Example 33

Synthesis of N$^\beta$-[1-(1-Thio-β-D-galactopyranosyl) cyclopent-3-yl]-β-alanine F7

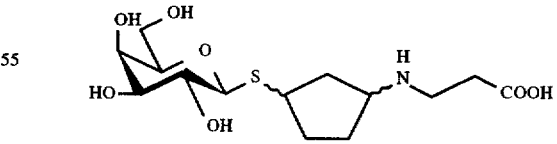

The title compound was prepared according to procedures D, H and M above using cyclopent-2-en-1-one as the electrophile and β-alanine tert-butyl ester as the amino acid ester. Mass spectra data was as follows: M (calcd.): 351.42; M (found): n.a. Selected nmr data was as follows: 1H-nmr (CD$_3$OD): δ 4.41, 4.40, and 4.38 (3 d, J 10 Hz), 3.17 and 2.52 (2 br s), 2.21 and 1.94 (2 m).

Example 34

Synthesis of N$^\beta$-|1-(1-Thio-β-D-galactopyranosyl)-6,6-methylcyclohex-3-yl|-β-alanine F9

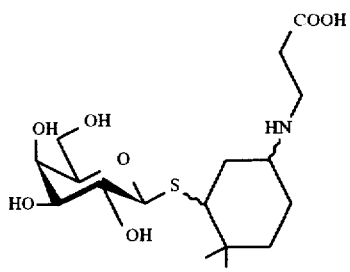

The title compound was prepared according to procedures D, H and M above using 4,4-dimethylcyclohex-2-en-1-one as the electrophile and β-alanine tert-butyl ester as the amino acid ester. Mass spectra data was as follows: M (calcd.): 393.50; M (found): 399.3 (M+H$^+$), 419.5 (M+Na$^+$), 442.4 (M+K$^+$).

Example 35

Synthesis of N$^\beta$-|1-(1-Thio-β-D-galactopyranosyl) cyclohex-3-yl|-β-alanine F10

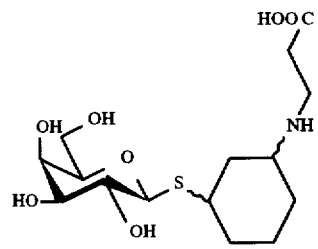

The title compound was prepared according to procedures D, H and M above using cyclohex-2-en-1-one as the electrophile and β-alanine tert-butyl ester as the amino acid ester. Mass spectra data was as follows: M (calcd.): 365.45; M (found): 389.9 (M+Na$^+$). Selected nmr data was as follows: 1H-nmr (CD$_3$OD): δ 4.45, 4.43, 4.42, and 4.36 (4 d, J 10 Hz), 3.18 and 2.47 (2 br s), 3.02, 2.56, 2.33, 2.07, 1.92, 1.81, 1.74, 1.50, and 1.34 (9 m).

Example 36

Synthesis of N$^\alpha$-|1-(1-Thio-β-D-galactopyranosyl) cyclohex-2-yl|-L-leucine G2

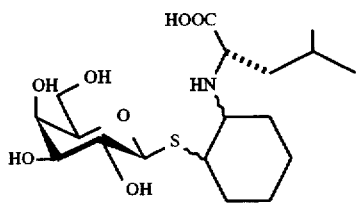

The title compound was prepared according to procedures D, H and M above using 2-chlorocyclohexanone as the electrophile and L-leucine tert-butyl ester as the amino acid ester. Mass spectra data was as follows: M (calcd.): 407.53; M (found): 410.9, (M+H$^+$), 435.5 (M+Na$^+$).

Example 37

Synthesis of N$^\alpha$-|1-(1-Thio-β-D-galactopyranosyl) cyclohept-3-yl|-L-leucine G5

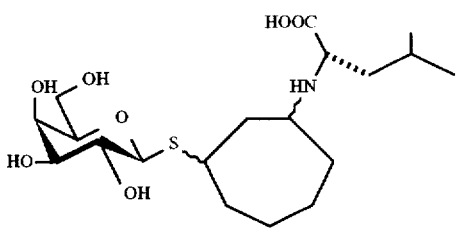

The title compound was prepared according to procedures D, H and M above using cyclohept-2-en-1-one as the electrophile and L-leucine tert-butyl ester as the amino acid ester. Mass spectra data was as follows: M (calcd.): 421.55; M (found): 421.7 (M+H$^+$), 448.0 (M+Na$^+$).

Example 38

Synthesis of N$^\alpha$-|1-(1-Thio-β-D-galactopyranosyl)-6 6-dimethylcyclohex-3-yl|-L-leucine G9

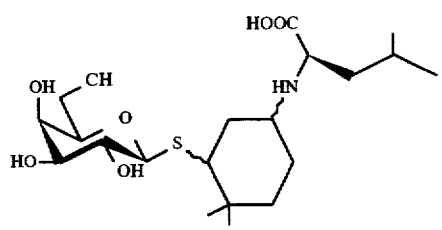

The title compound was prepared according to procedures D, H and M above using 4,4-dimethylcyclohex-2-en-1-one as the electrophile and L-leucine tert-butyl ester as the amino acid ester. Mass spectra data was as follows: M (calcd.): 436.58; M (found): 438.0 (M+H$^+$), 461.4 (M+Na$^+$).

Example 39

Synthesis of N$^\alpha$-|1-(1-Thio-β-D-galactopyranosyl) cyclohex-3-yl|-L-leucine G10

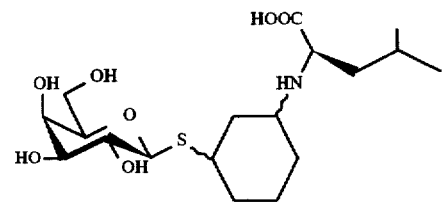

The title compound was prepared according to procedures D, H and M above using cyclohex-2-en-1-one as the electrophile and L-leucine tert-butyl ester as the amino acid ester. Mass spectra data was as follows: M (calcd.): 407.53; M (found): 408.4 (M+H$^+$).

Example 40

Synthesis of N$^\alpha$-|1-(1-Thio-β-D-galactopyranosyl) cyclohex-2-yl|-L-histidine H2

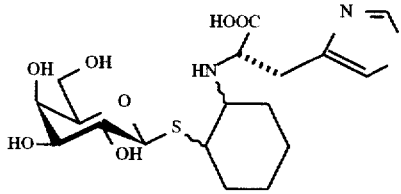

The title compound was prepared according to procedures D, H and N above using 2-chlorocyclohexanone as the electrophile and L-histidine methyl ester as the amino acid ester. Mass spectra data was as follows: M (calcd.): 431.50; M (found): 433.6 (M+H$^+$).

Example 41

Synthesis of N$^\alpha$-|1-(1-Thio-β-D-galactopyranosyl) cyclohept-3-yl|-L-histidine H5

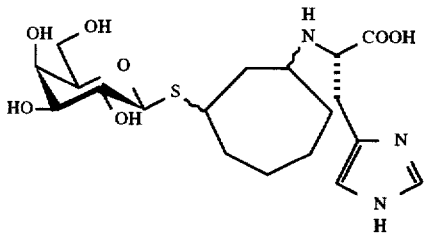

The title compound was prepared according to procedures D, H and N above using cyclohept-2-en-1-one as the electrophile and L-histidine methyl ester as the amino acid ester. Mass spectra data was as follows: M (calcd.): 445.54; M (found): 448.0 (M+H$^+$).

Example 42

Synthesis of N$^\alpha$-[1-(1-Thio-β-D-galactopyranosyl)-6,6-dimethylcyclohex-3-yl|-L-histidine H9

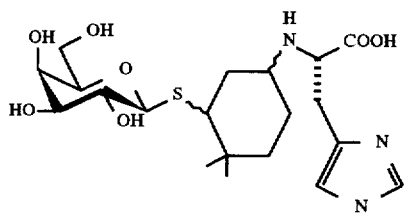

The title compound was prepared according to procedures D, H and N above using 4,4-dimethylcyclohex-2-en-1-one as the electrophile and L-histidine methyl ester as the amino acid ester. Mass spectra data was as follows: M (calcd.): 459.56; M (found): 462.2 (M+H$^+$).

Example 43

Synthesis of N$^\alpha$-|1-(1-Thio-β-D-galactopyranosyl) cyclohex-3-yl|-L-histidine H10

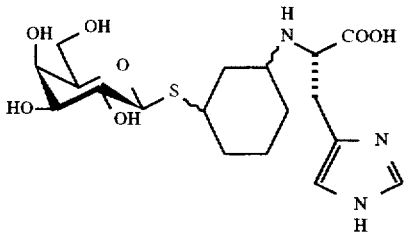

The title compound was prepared according to procedures D, H and N above using cyclohex-2-en-1-one as the electrophile and L-histidine methyl ester as the amino acid ester. Mass spectra data was as follows: M (calcd.): 431.51; M (found): 433.2 (M+H$^+$).

Example 44

Synthesis of N$^\alpha$-|1-(1-Thio-β-D-galactopyranosyl) cyclohex-2-yl|-L-tryptophan I2

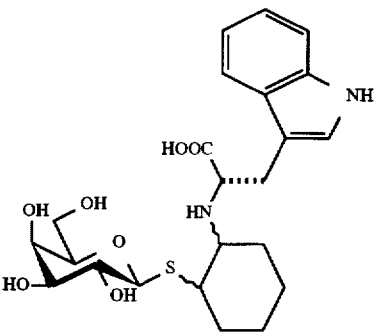

The title compound was prepared according to procedures D, H and N above using 2-chlorocyclohexanone as the electrophile and L-tryptophan methyl ester as the amino acid ester. Mass spectra data was as follows: M (calcd.): 480.59; M (found): 481.9 (M+H$^+$), 505.3 (M+Na$^+$).

Example 45

Synthesis of N$^\alpha$-|1-(1-Thio-β-D-galactopyranosyl) cyclohept-3-yl|-L-tryptophan I5

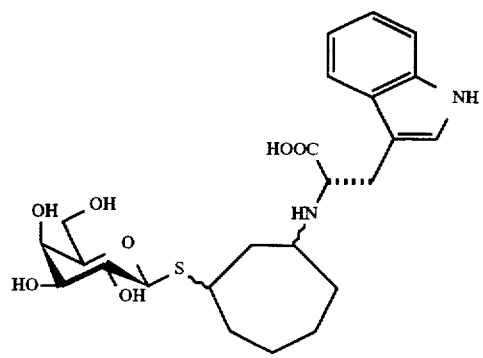

The title compound was prepared according to procedures D, H and N above using cyclohept-2-en-1-one as the electrophile and L-tryptophan methyl ester as the amino acid ester. Mass spectra data was as follows: M (calcd.): 480.58; M (found): 495.9 (M+H⁺).

Example 46

Synthesis of Nα-|1-(1-Thio-β-D-galactopyranosyl)-6,6-dimethylcyclohept-3-yl|-L-tryptophan I9

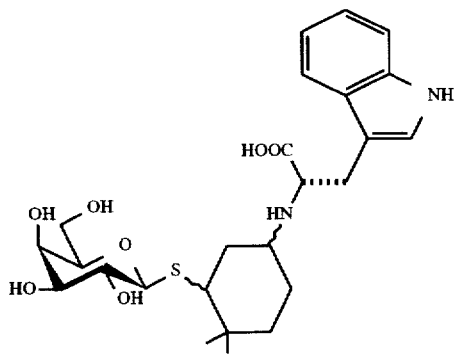

The title compound was prepared according to procedures D, H and N above using 4,4-dimethylcyclohex-2-en-1-one as the electrophile and L-tryptophan methyl ester as the amino acid ester. Mass spectra data was as follows: M (calcd.): 508.63; M (found): 512.1 (M+H⁺).

Example 47

Synthesis of Nα-|1-(1-Thio-β-D-galactopyranosyl) cyclohept-3-yl|-L-tryptophan I10

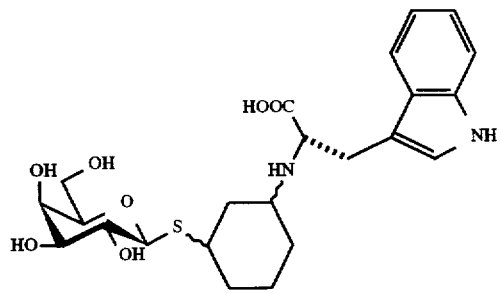

The title compound was prepared according to procedures D, H and N above using cyclohex-2-en-1-one as the electrophile and L-tryptophan methyl ester as the amino acid ester. Mass spectra data was as follows: M (calcd.): 480.59; M (found): 483.9 (M+H⁺).

Example 48

Synthesis of Nα-|1-(1-Thio-β-D-galactopyranosyl) cyclohex-2-yl|-L-arginine J2

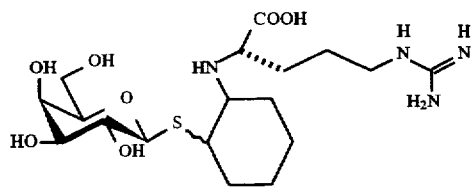

The title compound was prepared according to procedures D, H and O above using 2-chlorocyclopentanone as the electrophile and L-arginine methyl ester as the amino acid ester. Mass spectra data was as follows: M (calcd.): 450.56; M (found): 453.5 (M+H⁺).

Example 49

Synthesis of Nα-|1-(1-Thio-β-D-galactopyranosyl) cyclohept-3-yl|-L-arginine J5

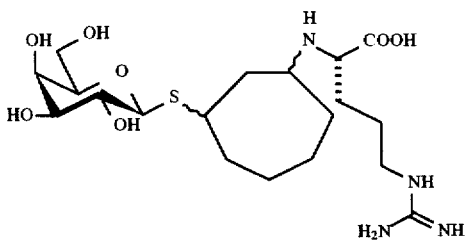

The title compound was prepared according to procedures D, H and O above using cyclohept-2-en-1-one as the electrophile and L-arginine methyl ester as the amino acid ester. Mass spectra data was as follows: M (calcd.): 464.58; M (found): 467.1 (M+H⁺).

Example 50

Synthesis of Nα-|1-(1-Thio-β-D-galactopyranosyl) cyclopent-3-yl|-L-arginine J7

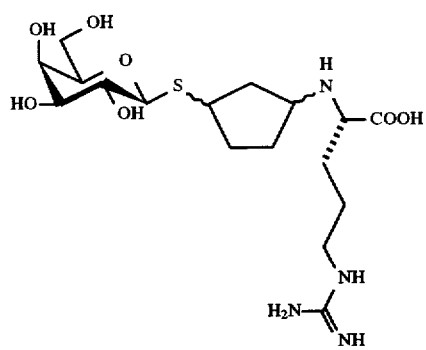

The title compound was prepared according to procedures D, H and O above using cyclopent-2-en-1-one as the electrophile and L-arginine methyl ester as the amino acid ester. Mass spectra data was as follows: M (calcd.): 436.53; M (found): n.a. Selected nmr data was as follows: 1H-nmr (CD₃OD): δ 4.18, 4.17, 4.16, and 4.15 (4 d, J 10 Hz), 3.90 (br d, J 3.6 Hz), 2.37, 2.04, and 1.53 (3 m).

Example 51

Synthesis of 4,4-Dimethyl-3-hydroxycyclohexyl 1-Thio-β-D-galactopyranoside A8

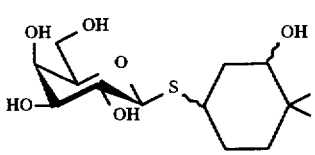

The title compound was prepared according to procedures D, E and I above using 6,6-dimethylcyclohex-2-en-1-one as the electrophile.

Example 52

Synthesis of 3-Amino-4,4-dimethylcyclohexyl 1-Thio-β-D-galactopyranoside B8

The title compound was prepared according to procedure D, F and J above using 6,6-dimethylcyclohex-2-en-1-one as the electrophile.

Example 53

Synthesis of 3-Acetamido-4,4-dimethylcyclohexyl 1-Thio-β-D-galactopyranoside C8

The title compound was prepared according to procedures D, F, J and K above using 6,6-dimethylcyclohex-2-en-1-one as the electrophile.

Example 54

Synthesis of $N^\alpha$-[1-(1-Thio-β-D-galactopyranosyl)-4,4-dimethylcyclohex-3-yl]-glycine E8

The title compound was prepared according to procedures D, H and M above using 6,6-dimethylcyclohex-2-en-1-one as the electrophile and glycine tert-butyl ester as the amino acid ester.

Example 55

Synthesis of $N^\beta$-[1-(1-Thio-β-D-galactopyranosyl)-4,4-methylcyclohex-3-yl]-β-alanine F8

The title compound was prepared according to procedures D, H and M above using 6,6-dimethylcyclohex-2-en-1-one as the electrophile and β-alanine tert-butyl ester as the amino acid ester.

Example 56

Inhibition of Heat-Labile Enterotoxin Binding to $G_{D1b}$

The 1-thiogalactose derivatives prepared above were tested for their ability to inhibit the binding of heat-labile enterotoxin from $E.$ $coli$ to ganglioside $G_{D1b}$. This bioassay was conducted using the procedure described by A.-M. Svennerholm[15] except that ganglioside $G_{D1b}$ was used instead of ganglioside $G_{M1}$. The results of this assay evidenced that each of the compounds of Examples 1, 3, 5, 8–18, 21, 22, 24–26, 29–33, 35, 37, 44, 45, 50–55 inhibited binding of heat-labile enterotoxin to ganglioside $G_{D1b}$ by at least 20%.

Example 57

Attachment of a Thiosaccharide to a Solid Support

To a solution of 1,2:3,4-di-O-isopropylidene-D-galactopyranose (1 eq.) in pyridine at room temperature is added succinic anhydride (1.2 eq.). The reaction is stirred overnight then concentrated in vacuo to give 1,2:3,4-di-O-isopropylidene-6-O-(3-carboxy)propanoyl-D-galactopyranose. To the residue is added 80% aqueous acetic acid to remove the isopropylidene groups. When this reaction is complete, the reaction mixture is concentrated in vacuo and to the residue is added excess 1:1 acetic anhydride/pyridine to afford 1,2,3,4-O-acetyl-6-O-(3-carboxy)propanoyl-D-galactopyranose. To this compound is then added excess thiolacetic acid in dry dichloromethane under argon at 0° C. and boron trifluoride etherate. The cold-bath is removed after 10 min and after 24 h the mixture is diluted with dichloromethane, washed with saturated sodium bicarbonate, dried over sodium sulfate, and concentrated to afford 1-S-acetyl-2,3,4-tri-O-acetyl-6-O-(3-carboxy)propanoyl-1-thio-α-D-galactopyranose. To this compound is added aminated Merrifield resin and a carbodimide coupling reagent to afford the O,S-protected galactopyranose coupled to the resin through the 6-O-(3-carboxy)propanoyl group.

From the foregoing description, various modifications and changes in the composition and method will occur to those skilled in the art. All such modifications coming within the scope of the appended claims are intended to be included therein.

What is claimed is:

1. A method for synthesizing a thiosaccharide derivative, which method comprises:
   (a) providing a thiosaccharide;
   (b) providing at least a stoichiometric amount of a coupling reagent selected from the group consisting of Michael acceptors and α-halocarbonyl compounds; and
   (c) contacting the thiosaccharide and the coupling reagent under conditions which provide for a thiosaccharide carbonyl compound.

2. The method of claim 1, which method further comprises the step of:
   (d) reducing the carbonyl group of the thiosaccharide carbonyl compound to form a group selected from hydroxy and amino derivatives.

3. A method for synthesizing a thiosaccharide derivative on a solid support, which method comprises:
   (a) providing a thiosaccharide;
   (b) providing at least a stoichiometric amount of a coupling reagent selected from Michael acceptors and α-halocarbonyl compounds wherein either the thiosaccharide or the coupling reagent is covalently attached to a solid support; and
   (c) contacting the thiosaccharide and the coupling reagent under conditions which provide for a thiosaccharide carbonyl compound covalently attached to a solid support.

4. The method of claim 1, which method further comprises the step of:
   (d) reducing the carbonyl group of the thiosaccharide carbonyl compound to form a group selected from hydroxy and amino derivatives.

5. A method for preparing a thiosaccharide derivative library produced by synthesizing on each of a plurality of solid supports a single compound wherein each compound comprises a thiosaccharide derivative, which library is synthesized in a process comprising:
   a) apportioning solid supports among a plurality of reaction vessels which supports comprise a reactive functional group covalently bound thereto which group is capable of covalently binding a thiosaccharide at a position other than the thiol group;
   b) contacting the supports in each reaction vessel with a unique thiosaccharide under conditions wherein the thiosaccharide is covalently attached to the solid supports through the reactive functional group;
   c) pooling the supports;
   d) apportioning the supports from (c) above among a plurality of reaction vessels; and
   e) contacting the supports in each reaction vessel from (d) above with a unique coupling reagent selected from the group consisting of Michael acceptors and α-halocarbonyl compounds under conditions which provide for a thiosaccharide carbonyl compound covalently bound to said support.

6. The method of claim 5, which method further comprises the steps of:
   (f) pooling the supports from procedure (e);
   (g) apportioning the supports from (f) above among a plurality of reaction vessels; and
   (h) reducing the carbonyl group of the thiosaccharide carbonyl compound to form a group selected from hydroxy and amino derivatives.

7. The method of claim 6, which method further comprises the steps of:
   (i) pooling the supports from procedure (h) above;
   (j) apportioning the supports from (i) above among a plurality of reaction vessels; and
   (k) derivatizing the hydroxyl or amine groups to form a functional group selected from esters, amides, carbamates, ureas, thioureas, thioesters and thiocarbamates.

8. A method for preparing a thiosaccharide derivative library produced by synthesizing on each of a plurality of solid supports a single compound wherein each compound comprises a thiosaccharide derivative, which library is synthesized in a process comprising:
   a) apportioning solid supports among a plurality of reaction vessels which supports comprise a reactive functional group covalently bound thereto which group is capable of covalently binding a coupling reagent;
   b) contacting the supports in each reaction vessel with a unique coupling reagent selected from the group consisting of Michael acceptors and α-halocarbonyl compounds under conditions wherein the coupling reagent is covalently attached to the solid supports through the reactive functional group;
   c) pooling the supports;
   d) apportioning the supports from (c) above among a plurality of reaction vessels; and
   e) contacting the supports in each reaction vessel from (d) above with a unique thiosaccharide under conditions which provide for a thiosaccharide carbonyl compound covalently bound to said support.

9. The method of claim 8, which method further comprises the steps of:
   (f) pooling the supports from procedure (e);
   (g) apportioning the supports from (f) above among a plurality of reaction vessels; and
   (h) reducing the carbonyl group of the thiosaccharide carbonyl compound to form a group selected from hydroxy and amino derivatives.

10. The method of claim 9, which method further comprises the steps of:
    (i) pooling the supports from procedure (h) above;
    (j) apportioning the supports from (i) above among a plurality of reaction vessels; and
    (k) derivatizing the hydroxyl or amine groups to form a functional group selected from esters, amides, carbamates, ureas, thioureas, thioesters and thiocarbamates.

11. A library of diverse thiosaccharide derivatives comprising a plurality of solid supports having a plurality of covalently bound thiosaccharides derivatives, wherein the thiosaccharide derivative bound to each of said supports is substantially homogeneous and further wherein the thiosaccharide derivative bound on one support is different from the thiosaccharide derivatives bound on the other supports and further wherein said thiosaccharide derivative is represented by the formula (I):

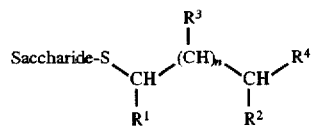

wherein $R^1$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I to the solid support;

$R^2$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I to the solid support;

$R^3$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I to the solid support;

wherein $R^1$ and $R^2$ or $R^1$ and $R^3$ or $R^2$ and $R^3$ can be joined, together with the carbon atoms to which $R^1$ and/or $R^2$ and/or $R^3$ are attached, to form a cycloalkyl ring, a cycloalkenyl ring, or a heterocyclic ring, provided that said heterocyclic ring is not a saccharide or an oligosaccharide;

$R^4$ is selected from the group consisting of —$XR^5$, —$XC(O)R^6$, —$XC(O)X'R^7$ and —$C(O)XR^8$;

wherein X and X' are each independently selected from the group consisting of oxygen, sulfur and —$NR^9$—, wherein $R^9$ is selected from the group consisting of hydrogen and alkyl;

$R^5$ is selected from the group consisting of hydrogen, alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I to the solid support, and when X is —$NR^9$—, then $R^9$ together with X can form an amino acid;

$R^6$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I to the solid support;

$R^7$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I to the solid support;

$R^8$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I to the solid support; and n is an integer equal to 0 or 1;

wherein the saccharide is selected from the group consisting of a monosaccharide, an oligosaccharide, monosaccharide-Y and oligosaccharide-Y, wherein Y is a linking arm covalently linking the compound of formula I to the solid support;

with the proviso that only one of $R^1$, $R^2$, $R^3$, $R^4$, $R^6$, $R^7$, $R^8$ and Y is linked to the solid support.

\* \* \* \* \*